(12) United States Patent
Demond et al.

(10) Patent No.: US 7,320,697 B2
(45) Date of Patent: Jan. 22, 2008

(54) ONE PIECE LOOP AND COIL

(75) Inventors: Jackson Demond, Santa Cruz, CA (US); Marlon C. Moreno, San Jose, CA (US); Robert L. Cassell, Otsego, MN (US); Peter Hirshman, Minneapolis, MN (US); Eliot T. Kim, Santa Clara, CA (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 552 days.

(21) Appl. No.: 10/730,232

(22) Filed: Dec. 8, 2003

(65) Prior Publication Data

US 2004/0116960 A1 Jun. 17, 2004

Related U.S. Application Data

(63) Continuation-in-part of application No. 09/764,774, filed on Jan. 16, 2001, now abandoned, which is a continuation-in-part of application No. 09/430,211, filed on Oct. 29, 1999, now Pat. No. 6,589,263, which is a continuation-in-part of application No. 09/364,064, filed on Jul. 30, 1999, now Pat. No. 6,530,939.

(51) Int. Cl.
*A61M 29/00* (2006.01)
*A61F 2/06* (2006.01)

(52) U.S. Cl. .................. 606/200; 623/1.23
(58) Field of Classification Search ........... 606/200; 623/1.23
See application file for complete search history.

(56) References Cited

U.S. PATENT DOCUMENTS 3,472,230 A 10/1969 Fogarty
3,592,186 A 7/1971 Oster
3,683,904 A 8/1972 Forster
3,889,657 A 6/1975 Baumgarten (Continued)

FOREIGN PATENT DOCUMENTS

DE 28 21 048 7/1980

(Continued)

OTHER PUBLICATIONS

"Atherosclerotic Disease of the Aortic Arch as a Risk Factor of Recurrent Ischemic Stroke," *The New England Journal of Medicine*, pp. 1216-1221 (May 1996).

(Continued)

*Primary Examiner*—Anhtuan T. Nguyen
*Assistant Examiner*—Timothy J Neal
(74) *Attorney, Agent, or Firm*—Crompton, Seager & Tufte LLC

(57) ABSTRACT

Apparatus and methods are provided for use in filtering emboli from a vessel, wherein a vascular filter is disposed on a guide wire, the vascular filter having a support hoop disposed from a suspension strut so as to permit lateral eccentric displacement of the support hoop relative to a longitudinal axis of the guide wire. A blood permeable sac is affixed to the support hoop to form a mouth of the blood permeable sac. The support hoop is disposed obliquely relative to the guide wire and is capable of being properly used in a wide range of vessel diameters. The support hoop collapses the mouth of the blood permeable sac during removal of the vascular filter to prevent material from escaping from the sac. A delivery sheath and introducer sheath for use with the vascular filter of the present invention are also provided.

58 Claims, 14 Drawing Sheets

U.S. PATENT DOCUMENTS

| | | |
|---|---|---|
| 3,952,747 A | 4/1976 | Kimmell, Jr. |
| 3,996,938 A | 12/1976 | Clark, III |
| 4,046,150 A | 9/1977 | Schwartz et al. |
| 4,425,908 A | 1/1984 | Simon |
| 4,447,227 A | 5/1984 | Kotsanis |
| 4,580,568 A | 4/1986 | Gianturco |
| 4,590,938 A | 5/1986 | Segura et al. |
| 4,619,246 A | 10/1986 | Molgaard-Nielsen et al. |
| 4,631,052 A | 12/1986 | Kensey |
| 4,643,184 A | 2/1987 | Mobin-Uddin |
| 4,650,466 A | 3/1987 | Luther |
| 4,662,885 A | 5/1987 | DiPisa, Jr. |
| 4,705,517 A | 11/1987 | DiPisa, Jr. |
| 4,706,671 A | 11/1987 | Weinrib |
| 4,723,549 A | 2/1988 | Wholey et al. |
| 4,728,319 A | 3/1988 | Masch |
| 4,733,665 A | 3/1988 | Palmaz |
| 4,790,812 A | 12/1988 | Hawkins, Jr. et al. |
| 4,790,813 A | 12/1988 | Kensey |
| 4,794,928 A | 1/1989 | Kletschka |
| 4,794,931 A | 1/1989 | Yock |
| 4,800,882 A | 1/1989 | Gianturco |
| 4,807,626 A | 2/1989 | McGirr |
| 4,842,579 A | 6/1989 | Shiber |
| 4,857,045 A | 8/1989 | Rydell |
| 4,857,046 A | 8/1989 | Stevens et al. |
| 4,867,157 A | 9/1989 | McGurk-Burleson et al. |
| 4,873,978 A | 10/1989 | Ginsburg |
| 4,898,575 A | 2/1990 | Fischell et al. |
| 4,907,336 A | 3/1990 | Gianturco |
| 4,921,478 A | 5/1990 | Solano et al. |
| 4,921,484 A | 5/1990 | Hillstead |
| 4,926,858 A | 5/1990 | Giffort, III et al. |
| 4,950,277 A | 8/1990 | Farr |
| 4,955,895 A | 9/1990 | Sugiyama et al. |
| 4,957,482 A | 9/1990 | Shiber |
| 4,969,891 A | 11/1990 | Gewertz |
| 4,979,951 A | 12/1990 | Simpson |
| 4,986,807 A | 1/1991 | Farr |
| 4,998,539 A | 3/1991 | Delsanti |
| 5,002,560 A | 3/1991 | Machold et al. |
| RE33,569 E | 4/1991 | Gifford, III et al. |
| 5,007,896 A | 4/1991 | Shiber |
| 5,007,917 A | 4/1991 | Evans |
| 5,011,488 A | 4/1991 | Ginsburg |
| 5,019,088 A | 5/1991 | Farr |
| 5,041,126 A | 8/1991 | Gianturco |
| 5,053,008 A | 10/1991 | Bajaj |
| 5,053,044 A | 10/1991 | Mueller et al. |
| 5,071,407 A | 12/1991 | Termin et al. |
| 5,071,425 A | 12/1991 | Gifford, III et al. |
| 5,085,662 A | 2/1992 | Willard |
| 5,087,265 A | 2/1992 | Summers |
| 5,100,423 A | 3/1992 | Fearnot |
| 5,100,424 A | 3/1992 | Jang et al. |
| 5,100,425 A | 3/1992 | Fischell et al. |
| 5,102,415 A | 4/1992 | Guenther et al. |
| 5,104,399 A | 4/1992 | Lazarus |
| 5,108,419 A | 4/1992 | Reger et al. |
| 5,133,733 A | 7/1992 | Rasmussen et al. |
| 5,135,531 A | 8/1992 | Shiber |
| 5,152,771 A | 10/1992 | Sabbaghian et al. |
| 5,152,777 A | 10/1992 | Goldberg et al. |
| 5,160,342 A | 11/1992 | Reger et al. |
| 5,171,233 A | 12/1992 | Amplatz et al. |
| 5,190,546 A | 3/1993 | Jervis |
| 5,195,955 A | 3/1993 | Don Michael |
| 5,224,953 A | 7/1993 | Morgentaler |
| 5,306,286 A | 4/1994 | Stack et al. |
| 5,314,444 A | 5/1994 | Gianturco |
| 5,314,472 A | 5/1994 | Fontaine |
| 5,318,576 A | 6/1994 | Plassche, Jr. et al. |
| 5,329,942 A | 7/1994 | Gunther et al. |
| 5,330,484 A | 7/1994 | Gunther |
| 5,330,500 A | 7/1994 | Song |
| 5,350,398 A | 9/1994 | Pavcnik et al. |
| 5,354,310 A | 10/1994 | Garnic et al. |
| 5,356,423 A | 10/1994 | Tihon et al. |
| 5,366,464 A | 11/1994 | Belknap |
| 5,366,473 A | 11/1994 | Winston et al. |
| 5,370,657 A | 12/1994 | Irie |
| 5,370,683 A | 12/1994 | Fontaine |
| 5,376,100 A | 12/1994 | Lefebvre |
| 5,383,887 A | 1/1995 | Nadal |
| 5,383,892 A | 1/1995 | Cardon et al. |
| 5,383,926 A | 1/1995 | Lock et al. |
| 5,387,235 A | 2/1995 | Chuter |
| 5,395,349 A | 3/1995 | Quiachon et al. |
| 5,397,345 A | 3/1995 | Lazerus |
| 5,405,377 A | 4/1995 | Cragg |
| 5,409,454 A | 4/1995 | Fischell et al. |
| 5,415,630 A | 5/1995 | Gory et al. |
| 5,419,774 A | 5/1995 | Willard et al. |
| 5,421,832 A | 6/1995 | Lefebvre |
| 5,423,742 A | 6/1995 | Theron |
| 5,423,885 A | 6/1995 | Williams |
| 5,425,765 A | 6/1995 | Tiefenbrun et al. |
| 5,443,498 A | 8/1995 | Fontaine |
| 5,449,372 A | 9/1995 | Schmaltz et al. |
| 4,842,579 A | 10/1995 | Shiber |
| 5,456,667 A | 10/1995 | Ham et al. |
| 5,462,529 A | 10/1995 | Simpson et al. |
| 5,476,104 A | 12/1995 | Sheahon |
| 5,484,418 A | 1/1996 | Quiachon et al. |
| 5,507,767 A | 4/1996 | Maeda et al. |
| 5,512,044 A | 4/1996 | Duer |
| 5,527,354 A | 6/1996 | Fontaine et al. |
| 5,536,242 A | 7/1996 | Willard et al. |
| 5,540,707 A | 7/1996 | Ressemann et al. |
| 5,549,626 A | 8/1996 | Miller et al. |
| 5,562,724 A | 10/1996 | Vowerk et al. |
| 5,569,274 A | 10/1996 | Rapacki et al. |
| 5,569,275 A | 10/1996 | Kotula et al. |
| 5,634,897 A | 6/1997 | Dance et al. |
| 5,658,296 A | 8/1997 | Bates et al. |
| 5,662,671 A | 9/1997 | Barbut et al. |
| 5,669,933 A | 9/1997 | Simon et al. |
| 5,695,519 A | 12/1997 | Summers et al. |
| 5,709,704 A | 1/1998 | Nott et al. |
| 5,720,764 A | 2/1998 | Naderlinger |
| 5,728,066 A | 3/1998 | Daneshvar |
| 5,746,758 A | 5/1998 | Nordgren et al. |
| 5,749,848 A | 5/1998 | Jang et al. |
| 5,769,816 A | 6/1998 | Barbut et al. |
| 5,779,716 A | 7/1998 | Cano et al. |
| 5,792,157 A | 8/1998 | Mische et al. |
| 5,792,300 A | 8/1998 | Inderbitzen et al. |
| 5,795,322 A | 8/1998 | Boudewijn |
| 5,797,952 A | 8/1998 | Klein |
| 5,800,457 A | 9/1998 | Gelbfish |
| 5,800,525 A | 9/1998 | Bachinski et al. |
| 5,810,874 A | 9/1998 | Lefebvre |
| 5,814,064 A | 9/1998 | Daniel et al. |
| 5,817,102 A | 10/1998 | Johnson et al. |
| 5,827,324 A | 10/1998 | Cassell et al. |
| 5,833,644 A | 11/1998 | Zadno-Azizi et al. |
| 5,833,650 A | 11/1998 | Imran |
| 5,846,260 A | 12/1998 | Maahs |
| 5,848,964 A | 12/1998 | Samuels |
| 5,876,367 A | 3/1999 | Kaganov et al. |
| 5,893,867 A | 4/1999 | Bagaoisan et al. |
| 5,895,399 A | 4/1999 | Barbut et al. |
| 5,902,263 A | 5/1999 | Patterson et al. |
| 5,906,618 A | 5/1999 | Larson, III |

| | | |
|---|---|---|
| 5,908,435 A | 6/1999 | Samuels |
| 5,910,154 A | 6/1999 | Tsugita et al. |
| 5,911,734 A | 6/1999 | Tsugita et al. |
| 5,916,193 A | 6/1999 | Stevens et al. |
| 5,925,016 A | 7/1999 | Chornenky et al. |
| 5,925,060 A | 7/1999 | Forber |
| 5,925,062 A | 7/1999 | Purdy |
| 5,925,063 A | 7/1999 | Khosravi |
| 5,928,203 A | 7/1999 | Davey et al. |
| 5,928,218 A | 7/1999 | Gelbfish |
| 5,934,284 A | 8/1999 | Plaia et al. |
| 5,935,139 A | 8/1999 | Bates |
| 5,938,645 A | 8/1999 | Gordon |
| 5,941,869 A | 8/1999 | Patterson et al. |
| 5,941,896 A | 8/1999 | Kerr |
| 5,947,995 A | 9/1999 | Samuels |
| 5,951,585 A | 9/1999 | Cathcart et al. |
| 5,954,745 A | 9/1999 | Gertler et al. |
| 5,976,172 A | 11/1999 | Homsma et al. |
| 5,980,555 A | 11/1999 | Barbut et al. |
| 5,989,210 A | 11/1999 | Morris et al. |
| 5,989,271 A | 11/1999 | Bonnette et al. |
| 5,989,281 A | 11/1999 | Barbut et al. |
| 5,993,469 A | 11/1999 | McKenzie et al. |
| 5,997,557 A | 12/1999 | Barbut et al. |
| 6,001,118 A | 12/1999 | Daniel et al. |
| 6,007,557 A | 12/1999 | Ambrisco et al. |
| 6,010,522 A | 1/2000 | Barbut et al. |
| 6,013,085 A | 1/2000 | Howard |
| 6,027,520 A | 2/2000 | Tsugita et al. |
| 6,042,598 A | 3/2000 | Tsugita et al. |
| 6,051,014 A | 4/2000 | Jang |
| 6,051,015 A | 4/2000 | Maahs |
| 6,053,932 A | 4/2000 | Daniel et al. |
| 6,059,814 A | 5/2000 | Ladd |
| 6,066,149 A | 5/2000 | Samson et al. |
| 6,066,158 A | 5/2000 | Engelson et al. |
| 6,068,645 A | 5/2000 | Tu |
| 6,086,605 A | 7/2000 | Barbut et al. |
| 6,117,154 A | 9/2000 | Barbut et al. |
| 6,129,739 A | 10/2000 | Khosravi |
| 6,136,016 A | 10/2000 | Barbut et al. |
| 6,142,987 A | 11/2000 | Tsugita |
| 6,152,946 A | 11/2000 | Broome et al. |
| 6,165,200 A | 12/2000 | Tsugita et al. |
| 6,168,579 B1 | 1/2001 | Tsugita |
| 6,171,327 B1 | 1/2001 | Daniel et al. |
| 6,171,328 B1 | 1/2001 | Addis |
| 6,179,851 B1 | 1/2001 | Barbut et al. |
| 6,179,859 B1 | 1/2001 | Bates et al. |
| 6,179,861 B1 | 1/2001 | Khosravi et al. |
| 6,187,025 B1 | 2/2001 | Machek |
| 6,203,561 B1 | 3/2001 | Ramee et al. |
| 6,206,868 B1 | 3/2001 | Parodi |
| 6,214,026 B1 | 4/2001 | Lepak et al. |
| 6,221,006 B1 | 4/2001 | Dubrul et al. |
| 6,224,620 B1 | 5/2001 | Maahs |
| 6,231,544 B1 | 5/2001 | Tsugita et al. |
| 6,235,044 B1 | 5/2001 | Root et al. |
| 6,235,045 B1 | 5/2001 | Barbut et al. |
| 6,238,412 B1 | 5/2001 | Dubrul et al. |
| 6,245,087 B1 | 6/2001 | Addis |
| 6,245,088 B1 | 6/2001 | Lowery |
| 6,245,089 B1 | 6/2001 | Daniel et al. |
| 6,258,115 B1 | 7/2001 | Dubrul |
| 6,264,663 B1 | 7/2001 | Cano |
| 6,264,672 B1 | 7/2001 | Fisher |
| 6,270,513 B1 | 8/2001 | Tsugita et al. |
| 6,277,138 B1 | 8/2001 | Levinson et al. |
| 6,277,139 B1 | 8/2001 | Levinson et al. |
| 6,280,413 B1 | 8/2001 | Clark et al. |
| 6,287,321 B1 | 9/2001 | Jang |
| 6,290,710 B1 | 9/2001 | Cryer et al. |
| 6,309,399 B1 | 10/2001 | Barbut et al. |
| 6,319,268 B1 | 11/2001 | Ambrisco et al. |
| 6,344,049 B1 | 2/2002 | Levinson et al. |
| 6,361,545 B1 * | 3/2002 | Macoviak et al. ......... 606/200 |
| 6,371,971 B1 | 4/2002 | Tsugita et al. |
| 6,425,909 B1 * | 7/2002 | Dieck et al. ................ 606/200 |
| 6,540,722 B1 | 4/2003 | Boyle et al. |
| 6,544,279 B1 | 4/2003 | Hopkins et al. |
| 6,544,280 B1 | 4/2003 | Daniel et al. |
| 6,569,184 B2 | 5/2003 | Huter |
| 6,575,996 B1 | 6/2003 | Denison et al. |
| 6,589,263 B1 | 7/2003 | Hopkins et al. |
| 6,602,271 B2 | 8/2003 | Adams et al. |
| 6,605,102 B1 | 8/2003 | Mazzocchi et al. |
| 6,616,682 B2 | 9/2003 | Joergensen et al. |
| 6,620,182 B1 | 9/2003 | Khosravi et al. |
| 6,635,070 B2 | 10/2003 | Leeflang et al. |
| 6,645,224 B2 | 11/2003 | Gilson et al. |
| 6,893,451 B2 * | 5/2005 | Cano et al. ................. 606/200 |
| 2002/0022858 A1 | 2/2002 | Demond et al. |
| 2002/0095171 A1 | 7/2002 | Belef |
| 2002/0183783 A1 | 12/2002 | Shadduck |
| 2003/0004539 A1 | 1/2003 | Linder et al. |
| 2003/0078519 A1 | 4/2003 | Salahieh et al. |
| 2003/0163064 A1 | 8/2003 | Vrba et al. |
| 2003/0171770 A1 | 9/2003 | Kusleika et al. |
| 2003/0191493 A1 | 10/2003 | Epstein et al. |
| 2003/0208224 A1 | 11/2003 | Broome |

FOREIGN PATENT DOCUMENTS

| | | |
|---|---|---|
| DE | 34 17 738 | 11/1985 |
| DE | 40 30 998 A1 | 10/1990 |
| EP | 0 200 688 | 11/1986 |
| EP | 0 293 605 A1 | 12/1988 |
| EP | 0 411 118 A1 | 2/1991 |
| EP | 0 427 429 A2 | 5/1991 |
| EP | 0 437 121 B1 | 7/1991 |
| EP | 0 472 334 A1 | 2/1992 |
| EP | 0 472 368 A2 | 2/1992 |
| EP | 0 533 511 A1 | 3/1993 |
| EP | 0 655 228 A1 | 11/1994 |
| EP | 0 686 379 A2 | 6/1995 |
| EP | 0 696 447 A2 | 2/1996 |
| EP | 0 737 450 A1 | 10/1996 |
| EP | 0 743 046 A1 | 11/1996 |
| EP | 0 759 287 A1 | 2/1997 |
| EP | 0 771 549 A2 | 5/1997 |
| EP | 0 784 988 A1 | 7/1997 |
| EP | 0 852 132 A1 | 7/1998 |
| EP | 0 934 729 | 8/1999 |
| FR | 2 580 504 | 10/1986 |
| FR | 2 643 250 A1 | 8/1990 |
| FR | 2 666 980 | 3/1992 |
| FR | 2 768 326 A1 | 3/1999 |
| GB | 2 020 557 B | 1/1983 |
| JP | 8-187294 A | 7/1996 |
| SU | 764684 | 9/1980 |
| WO | WO 88/09683 | 12/1988 |
| WO | WO 92/03097 | 3/1992 |
| WO | WO 94/14389 | 7/1994 |
| WO | WO 94/24946 | 11/1994 |
| WO | WO 96/01591 | 1/1996 |
| WO | WO 96/10375 | 4/1996 |
| WO | WO 96/19941 | 7/1996 |
| WO | WO 96/23441 | 8/1996 |
| WO | WO 96/33677 | 10/1996 |
| WO | WO 97/17100 | 5/1997 |
| WO | WO 97/27808 | 8/1997 |
| WO | WO 97/42879 | 11/1997 |
| WO | WO 98/02084 | 1/1998 |
| WO | WO 98/02112 | 1/1998 |
| WO | WO 98/23322 | 6/1998 |

| | | |
|---|---|---|
| WO | WO 98/33443 | 8/1998 |
| WO | WO 98/34673 | 8/1998 |
| WO | WO 98/36786 | 8/1998 |
| WO | WO 98/38920 | 9/1998 |
| WO | WO 98/38929 | 9/1998 |
| WO | WO 98/39046 | 9/1998 |
| WO | WO 98/39053 | 9/1998 |
| WO | WO 98/39053 A1 | 9/1998 |
| WO | WO 98/46297 | 10/1998 |
| WO | WO 98/47447 | 10/1998 |
| WO | WO 98/49952 | 11/1998 |
| WO | WO 98/50103 | 11/1998 |
| WO | WO 98/51237 | 11/1998 |
| WO | WO 98/55175 | 12/1998 |
| WO | WO 99/09895 | 3/1999 |
| WO | WO 99/22673 | 5/1999 |
| WO | WO 99/23976 | 5/1999 |
| WO | WO 99/25252 | 5/1999 |
| WO | WO 99/30766 | 6/1999 |
| WO | WO 99/40964 | 8/1999 |
| WO | WO 99/42059 | 8/1999 |
| WO | WO 99/44510 | 9/1999 |
| WO | WO 99/44542 | 9/1999 |
| WO | WO 99/55236 | 11/1999 |
| WO | WO 99/58068 | 11/1999 |
| WO | WO 00/07655 | 2/2000 |
| WO | WO 00/09054 | 2/2000 |
| WO | WO 00/16705 | 3/2000 |
| WO | WO 00/49970 | 8/2000 |
| WO | WO 03/055413 A2 | 7/2003 |

OTHER PUBLICATIONS

"Endovascular Grafts, Stents Drive Interventional Radiology Growth," *Cardiovascular Device Update*, 2(3):1-12 (Mar. 1996).
"Protruding Atheromas in the Thoracic Aortic and Systemic Embolization," pp. 423-427 American College of Physicians (1991).
"Recognition and Embolic Potential of Intraaortic Atherosclerotic Debris," American College of Cardiology (Jan. 1991).
Cragg, Andrew et al., "A New Percutaneous Vena Cava Filger," *AJR*, 141:601-604 (Sep. 1983).
Cragg, Andrew et al., "Nonsurgical Placement of Arterial Endoprosthesis: A New Technique Using Nitinol Wire," *AJR*, pp. 261-263 (Apr. 1983).
Diethrich et al., "Percutaneous Techniques for Endoluminal Carotid Interventions," *J. Endovasc. Surg.*, 3:182-202 (1996).
Fadali, A. Moneim, "A filtering device for the prevention of particulate embolization during the course of cardiac surgery," *Surgery*, 64(3):634-639 (Sep. 1968).
Haissaguerre et al., "Spontaneous Initiation of Atrial Fibrillation by Ectopic Beats Originating in the Pulmonary Veins," *The New England Journal of Medicine*, 339(10):659-666 (Sep. 1988).
Jordan, Jr. et al., "Microemboli Detected by Transcranial Doppler Monitoring . . . ," *Cardiovascular Surgery*, 7(1)33-38 (Jan. 1999).
Lesh, "Can Catheter Ablation Cure Atrial Fibrillation?" *ACC Current Journal Review*, pp. 38-40 (Sep./Oct. 1997).
Lund et al., "Long-Term Patentcy of Ductus Arteriosus After Balloon Dilation: an Experimental Study," *Laboratory Investigation*, 69(4):772-774 (Apr. 1984).
Marache et al., "Percutaneous Transluminal Venous Angioplasty . . . ," *American Heart Journal*, 125(2 Pt 1):362-366 (Feb. 1993).
Mazur et al., "Directional Atherectomy with the Omnicath™: A Unique New Catheter System," *Catheterization and Cardiovascular Diagnosis*, 31:17-84 (1994).
Moussa, MD, Issaam "Stents Don't Require Systemic Anticoagulation . . . But the Technique (and Results) Must be Optimal," *Journal of Invasive Cardiol.*, 8(E):3E-7E, (1996).
Nakanishi et al., "Catheter Intervention to Venous System Using Expandable Metallic Stents," *Rinsho Kyobu Geka*, 14(2):English Abstract Only (Apr. 1994).
Onal et al., "Primary Stenting for Complex Atherosclerotic Plaques in Aortic and Iliac Stenoses," *Cardiovascular & Interventional Radiology*, 21(5):386-392 (1998).
Theron et al., "New Triple Coaxial Catheter System for Carotid Angioplasty with Cerebral Protection," *American Journal of Neuroradiology*, 11:869-874 (1990).
Tunick et al., "Protruding atherosclerotic plaque in the aortic archo f patients with systemic embolization: A new finding seen by transesophageal echocardiography," *American Heart Journal* 120(3):658-660 (Sep. 1990).
Waksman et al., "Distal Embolization is Common After Directional Atherectomy . . . ," *American Heart Journal*, 129(3):430-435 (1995).
Wholey, Mark H. et al., PTA and Stents in the Treatment of Extracranial Circulation, *The Journal of Invasive Cardiology*, 8(E):25E-30E (1996).

* cited by examiner

ONE PIECE LOOP AND COIL

REFERENCE TO RELATED APPLICATIONS

This application is a continuation-in-part of U.S. patent application Ser. No. 09/764,774 filed Jan. 16, 2001, now abandoned; which is in turn a continuation-in-part of U.S. patent application Ser. No. 09/430,211 filed Oct. 29, 1999, now U.S. Pat. No. 6,589,263; which is a continuation-in-part of U.S. patent application Ser. No. 09/364,064 filed Jul. 30, 1999, now U.S. Pat. No. 6,530,939.

FIELD OF THE INVENTION

The present invention relates to apparatus and methods for filtering or removing matter from within a vascular system. More particularly, the present invention provides a low profile self-expanding vascular device useful for capturing emboli or foreign bodies generated during interventional procedures.

BACKGROUND OF THE INVENTION

Percutaneous interventional procedures to treat occlusive vascular disease, such as angioplasty, atherectomy and stenting, often dislodge material from the vessel walls. This dislodged material, known as emboli, enters the bloodstream, and may be large enough to occlude smaller downstream vessels, potentially blocking blood flow to tissue. The resulting ischemia poses a serious threat to the health or life of a patient if the blockage occurs in critical tissue, such as the heart, lungs, or brain. The deployment of stents and stent-grafts to treat vascular disease, such as aneurysms, also involves introduction of foreign objects into the bloodstream, and also may result in the formation of clots or release of emboli. Such particulate matter, if released into the bloodstream, also may cause infarction or stroke.

Furthermore, interventional procedures may generate foreign bodies that are left within a patient's bloodstream, thereby endangering the life of the patient. Foreign bodies may include, for example, a broken guide wire, pieces of a stent, or pieces of a catheter.

Numerous previously known methods and apparatus have been proposed to reduce complications associated with embolism, release of thrombus, or foreign body material generation. U.S. Pat. No. 5,833,644 to Zadno-Azizi et al., for example, describes the use of a balloon-tipped catheter to temporarily occlude flow through a vessel from which a stenosis is to be removed. Stenotic material removed during a treatment procedure is evacuated from the vessel before the flow of blood is restored. A drawback of such previously known systems, however, is that occlusion of antegrade flow through the vessel may result in damage to the tissue normally fed by the blocked vessel.

U.S. Pat. No. 5,814,064 to Daniel et al. describes an emboli filter system having a radially expandable mesh filter disposed on the distal end of a guide wire. The filter is deployed distal to a region of stenosis, and an interventional device, such as angioplasty balloon or stent delivery system, is advanced along the guide wire. The filter is designed to capture emboli generated during treatment of the stenosis while permitting blood to flow through the filter. Similar filter systems are described in U.S. Pat. No. 4,723,549 to Wholey et al. and U.S. Pat. No. 5,827,324 to Cassell et al.

One disadvantage of radially expandable filter systems such as described in the foregoing patents is the relative complexity of the devices, which typically include several parts. Connecting more than a minimal number of such parts to a guide wire generally increases delivery complications. The ability of the guide wire to negotiate tortuous anatomy is reduced, and the profile of the device in its delivery configuration increases. Consequently, it may be difficult or impossible to use such devices in small diameter vessels, such as are commonly found in the carotid artery and cerebral vasculature. Moreover, such filter devices are generally incapable of preventing material from escaping from the filter during the process of collapsing the filter for removal.

Umbrella-type filter systems, such as described, for example, in U.S. Pat. No. 6,152,946 to Broome et al., also present additional drawbacks. One disadvantage of such systems is that the filters have only a limited range of operating sizes. Accordingly, a number of different filters of different sizes must be available to the clinician to treat different anatomies. Still further, such filters generally do not maintain apposition to the vessel wall when blood pressure pulses pass along a vessel, e.g., due to systole. In this case, because a blood pressure pulse can cause local swelling of the vessel diameter, the pressure pulse can cause the vessel to momentarily become lifted off the perimeter of the filter, thereby permitting emboli to bypass the filter.

International Publication No. WO 98/39053 describes a filter system having an elongated member, a radially expandable hoop and a cone-shaped basket. The hoop is affixed to the elongated member, and the cone-shaped basket is attached to the hoop and the elongated member, so that the hoop forms the mouth of the basket. The filter system includes a specially configured delivery catheter that retains the mouth of the basket in a radially retracted position during delivery.

While the filter system described in the foregoing International Publication reduces the number of components used to deploy the cone-shaped basket, as compared to the umbrella-type filter elements described hereinabove, it too has drawbacks. One such drawback is that because the hoop is fixed directly to the guide wire, the cone-shaped basket may not be fully deployable in a tortuous vessel. This problem is expected to arise, for example, where the resistance of the elongated member to bend to accommodate the tortuosity of the vessel causes the hoop and basket to be lifted away from the vessel wall, thereby providing a path for emboli-laden blood to bypass the filter.

Due to the eccentric nature in which the hoop is fastened to the elongated member in the foregoing International Application, it is expected that the perimeter of the hoop may be lifted away from the vessel wall when devices employing concentric lumens, e.g., angioplasty catheters or stent delivery systems, are brought in proximity of the filter.

Moreover, because the hoop in the aforementioned reference is directly fastened to the elongated member, there is also a risk that the basket will collapse or become wound around the elongated member due to twisting of the elongated member, e.g., during transluminal insertion of the filter, or during manipulation of the proximal end of the elongated member during insertion or withdrawal of interventional devices along the elongated member.

Furthermore, the method for flexibly attaching the filter hoop to the elongated member poses additional challenges. As discussed in the foregoing, if the filter is rigidly affixed directly to the elongated member, then the maneuverability required in accommodating tortuous vessels is compromised. Also, if the filter assembly is not properly attached to the elongated member, then the filter may become disengaged, thereby posing additional risks.

In view of the foregoing disadvantages of previously known apparatus and methods, it would be desirable to provide a vascular device, e.g., for use as a vascular filter, that overcomes such disadvantages and employs few components.

SUMMARY OF THE INVENTION

It is an object of the present invention to provide a reliable vascular filter that is capable of being fully deployed in tortuous anatomy.

It is another object of this invention to provide a vascular filter that is capable of spanning a range of vessel sizes, thereby reducing inventory requirements.

It is also an object of the present invention to provide a vascular filter that is resistant to becoming disengaged from the vessel wall due to lateral movements of the guide wire to which the vascular filter is coupled.

It is a further object of the present invention to provide a vascular filter that is resistant to becoming disengaged from the vessel wall due to local swelling of the vessel diameter as blood pressure pulses along the vessel past the filter deployment location.

It is another object of the present invention to provide a vascular filter that is resistant to collapse or disengagement from the vessel wall due to torsional forces applied to the guide wire to which the vascular filter is coupled.

It is a further object of the present invention to provide a vascular device that is capable of being contracted to a small delivery profile, thus permitting use of the device in vessels having relatively small diameters.

It is also an object of the present invention to provide methods for flexibly attaching the vascular filter to the elongated member.

These and other objects of the present invention are accomplished by providing a vascular device, suitable for use as a vascular filter, that has a blood permeable sac affixed at its perimeter to a support hoop. In accordance with an embodiment of the present invention, the support hoop is attached to a distal region of an elongated member, such as a guide wire, via one or more suspension strut which permits the guide wire to rotate and move laterally relative to the support hoop, without the support hoop becoming disengaged from the vessel wall. The support hoop supports a proximally-oriented mouth of the blood permeable sac when the device is deployed in a vessel. The device also may have a nose cone to facilitate percutaneous introduction, and a delivery sheath having one or more lumens.

In one embodiment, the suspension strut may include a support tube disposed concentrically over the guide wire that permits the guide wire to rotate relative to the support tube without transmitting torsional forces to the filter. In addition, the support hoop may include a linear or curved flexible suspension strut that holds the support hoop at near concentric position relative to the guide wire, thereby permiting large lateral deflections of the guide wire without the guide wire contacting the support hoop.

In alternative embodiments, the one or more suspension strut may further consist coils formed to enhance apposition of the support hoop to the vessel walls, or a nose cone mounted on the support tube. As a further alternative, the suspension strut may be configured as series of loops or coil turns in the guide wire proximal to the point of attachment of the support hoop, thereby isolating the filter from lateral or torsional disturbances applied at the proximal end of the guide wire. In still other alternative embodiments, sac bunching may be mitigated by tapering the sac or attaching it to the support tube.

A single use delivery sheath and introducer sheath suitable for use with the vascular filter of the present invention are also provided, as are methods of using the embodiments of the present invention.

BRIEF DESCRIPTION OF THE DRAWINGS

FIGS. 6A-6B are detailed views of the one or more suspension strut and nose cone construction of the embodiment of FIG. 3, while

DETAILED DESCRIPTION OF THE INVENTION

Figure 1A:
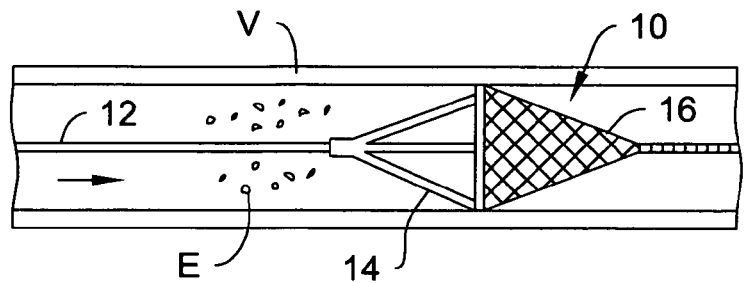
FIGS. 1A-1C are, respectively, side and ends view of an illustrative previously known vascular filter shown deployed in a straight length of vessel.

The above and other objects and advantages of the present invention will be apparent upon consideration of the following detailed description, taken in conjunction with the accompanying drawings, in which like reference characters refer to like parts throughout, and in which:

Referring to FIGS. 1A-1C and 2, some of the disadvantages of previously known umbrella-type filters are described as context for the benefits achievable with the vascular filter of the present invention. FIG. 1A shows a previously known umbrella-type filter 10 deployed in a straight length of vessel V, with emboli E approaching with antegrade flow. Filter 10 is disposed on guide wire 12 and includes one or more radially extending suspension strut 14 supporting biocompatible mesh 16.

Figure 1B:
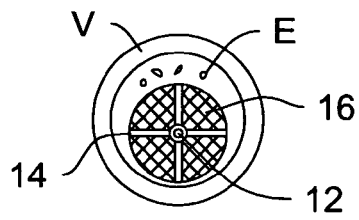

FIG. 1B illustrates a situation that may arise wherein the clinician underestimates the diameter of vessel V and deploys an undersized vascular filter 10. Because umbrella-type filters generally are capable of spanning only a narrow range of vessel diameters, the result as depicted in FIG. 1B may occur where filter 10 is undersized for the vessel diameter. In this case, emboli E will bypass around the edges of filter 10. Where umbrella-type filters of the kind depicted in FIG. 1 are used, the clinician must therefore exercise great care in selecting the appropriate filter size, and the hospital must carry a range of sizes to fit different patient anatomies.

Moreover, even where the clinician has selected a vascular filter appropriate for the nominal diameter of vessel V, bypass of emboli may still arise. This may occur, for example, where the vessel is subject to localized swelling as blood pressure pulses, e.g., during systole, pass along the length of the vessel. In this case, which has been observed to occur, for example, in the carotid arteries, the vessel wall may be momentarily lifted away from the perimeter of the vascular filter 10, resulting in a bypass situation similar to that depicted in FIG. 1B.

Figure 1C:
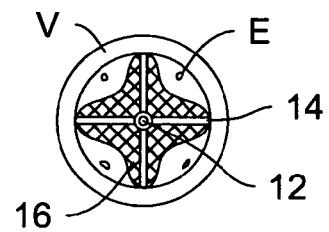

FIG. 1C depicts the situation that may occur where the clinician overestimates the diameter of vessel V, and selects filter 10 having a deployed diameter larger than the nominal vessel diameter. As illustrated in FIG. 1C, because suspension strut 14 contacts the interior surface of the vessel before becoming fully deployed, filter mesh 16 may be incompletely brought into apposition with the vessel wall around its circumference. Consequently, as depicted in FIG. 1C, folds may occur in filter mesh 16 that permit emboli E to once again bypass the filter.

Figure 2:
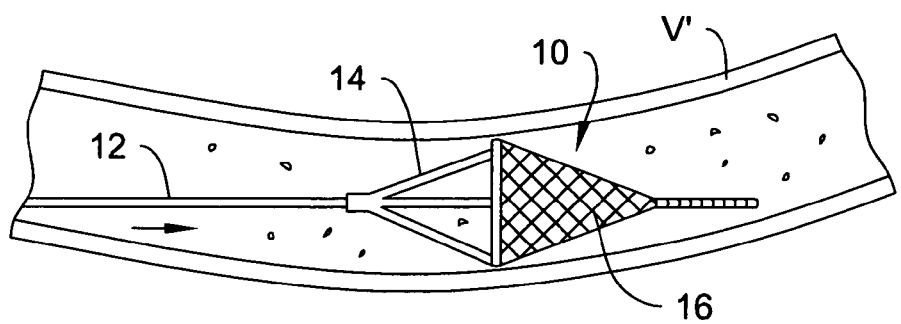
FIG. 2 is a side view of the vascular filter of FIG. 1 shown deployed in a tortuous vessel, where the stiffness of the guide wire causes the filter to partially collapse.

Referring now to FIG. 2, another drawback of the previously known vascular filters is described, which drawback is common to both umbrella-type and single fixed hoop type disclosed in the aforementioned International Publication WO 98/39053. This problem manifests where vascular filter 10 is inserted into tortuous anatomy, and in particular, where it is necessary to place the filter in or near curved vessel V', such as in smaller coronary arteries and the renal arteries.

As depicted in FIG. 2, guide wire 12 on which vascular filter 10 is disposed spans the bend in vessel V'. Due to the stiffness of guide wire 12 relative to suspension strut 14 of filter 10, when inserted in vessel bend having a small radius of curvature, suspension strut 14 may become compressed against the inner bend surface of vessel V'. This load may in turn prevent filter 10 from fully opening (or partially collapsing the effected suspension strut), permitting emboli to bypass the filter at the outer side of the bend.

Figure 3:
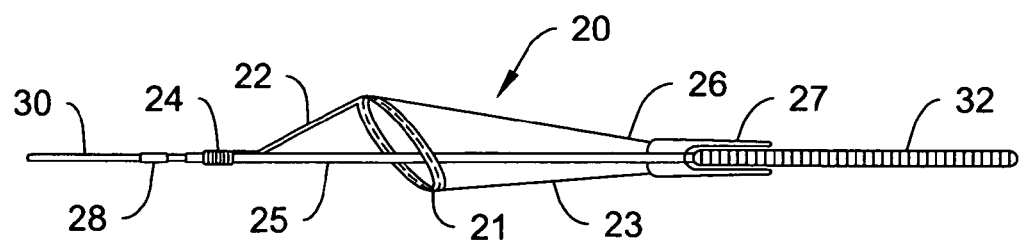
FIG. 3 is a side view of a vascular filter constructed in accordance with an embodiment of the present invention.

Referring now to FIG. 3, illustrative vascular filter 20 of an embodiment of the present invention is described. Filter 20 solves the above-described disadvantages by providing a filter that is expected to maintain apposition to a vessel wall even when used in tortuous vessels, vessels of uncertain size and those subject to localized temporal swelling caused by pressure pulsations.

Filter 20 may include self-expanding support hoop 21 mounted on suspension strut 22, and supporting blood permeable sac 23. Blood permeable sac 23 could be made from a biocompatible polymeric material having a plurality of pores. In one embodiment of the present invention, proximal end of suspension strut 22 may be affixed to tube 25 by forming a helix 24 around tube 25. Distal end 26 of blood permeable sac 23 is possibly mounted to nose cone 27, which in turn may be mounted to tube 25. As such, tube 25 could permit guide wire 30 to rotate independently of filter 20, thereby permitting floppy tip 32 of guide wire 30 to be directed within the vessel without causing blood permeable sac 23 to become wrapped around guide wire 30. In an alternate embodiment of the present invention, suspension strut 22 could be entwined around guide wire 30, thereby forming a helix at proximal end 24, and distal end 26 of blood permeable sac 23 is possibly mounted to nose cone 27, which in turn may be mounted to guide wire 30. Helix 24 may be prevented from untwining, for example, by using biocompatible material for welding, crimping, tieing or other bonding method. In this alternate embodiment, tube 25 is not required, and helix 24 having guide wire 30 passing therethrough, could permit guide wire 30 to rotate independently of filter 20. In either embodiment, filter 20 may be positioned between proximal stop 28 and enlarged floppy tip 32 of guide wire 30, which could function as a distal stop.

Figure 4A:
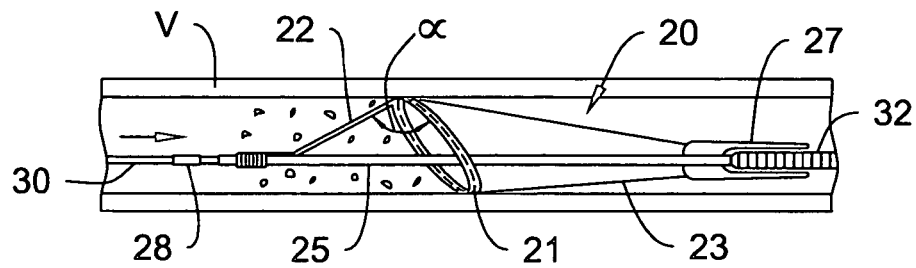
FIGS. 4A-4C are, respectively, side views of the vascular filter of FIG. 3 shown deployed in straight lengths of vessel of different diameters and in a tortuous vessel.
Figure 4B:
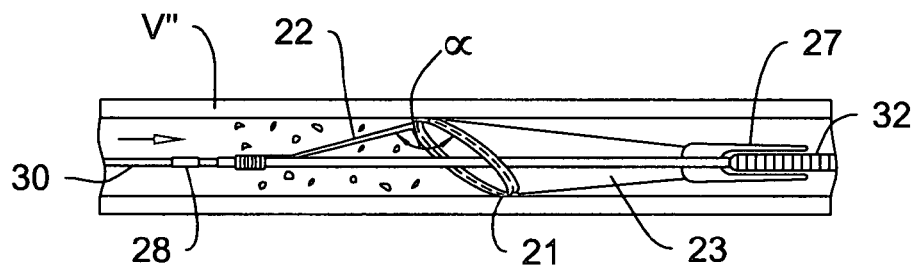
Figure 4C:
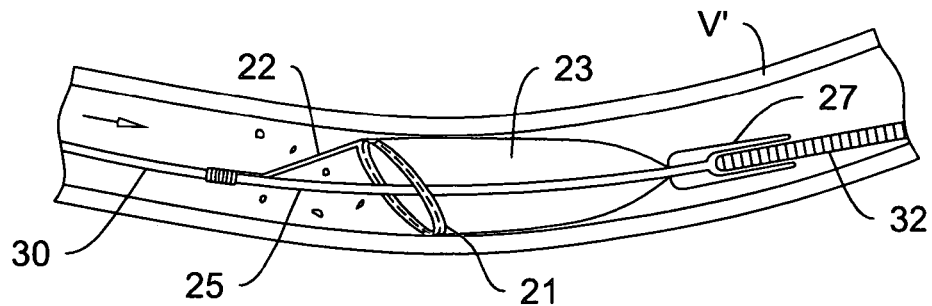

In one embodiment of the present invention, suspension strut 22 may position support hoop 21 approximately concentric to guide wire 30 when disposed in a substantially straight length of vessel, as depicted in FIG. 4A, but could permit the support hoop to become eccentrically displaced relative to guide wire 30 when the filter is deployed in a curved vessel, as depicted in FIG. 4C. Thus, unlike the case described above with respect to FIG. 2, the relative differences in stiffness between guide wire 30 and suspension strut 22 may facilitate, rather than impede, proper deployment of filter 20 by possibly permitting support hoop 21 to become eccentrically displaced relative to guide wire 30.

Referring now to FIGS. 4A and 4B, one advantage of the vascular filter of the present invention will be described. As depicted in FIG. 4A, support hoop 21 may be disposed obliquely, rather than radially, relative to the longitudinal axis of the vessel. Importantly, this arrangement could permit support hoop 21 to be used in vessels of different sizes.

In a larger diameter vessel, as depicted in FIG. 4A, angle α formed between suspension strut 22 and support hoop 21 may become less oblique, and support hoop 21 could be less elongated and nearly perpendicular to the vessel axis. By comparison, in a smaller diameter vessel depicted in FIG. 4B, angle α may become more oblique, and support hoop 21 could become more elongated and nearly parallel to the axis of the vessel. Filter 20 has been observed to retain adequate engagement with the vessel wall around the filter circumference over a wide range of vessel sizes. Accordingly, filter 20 may properly be used in a much wider range of vessel sizes than an umbrella-type filters, while providing superior apposition to the vessel walls. Thus, for example, a filter having a nominal diameter of 6 mm may be used in vessels having diameters between about 2.5 and 6.0 mm.

Figure 5:
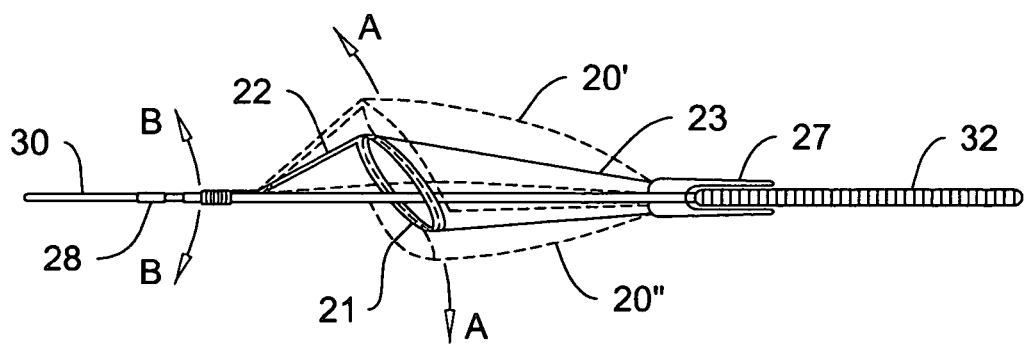
FIG. 5 is a side view illustration of the one or more suspension strut of an embodiment of the present invention permitting torsional and lateral movement of the guide wire without displacing the support hoop or filter sac.

Referring now to FIGS. 4C and 5, the use of flexible suspension strut 22 could permits the vascular filter to achieve good apposition to the vessel wall even in curved vessels, such as vessel V'. As shown in FIG. 5, vascular filter 20 may be capable of a wide range of eccentric lateral displacements in the direction shown by arrows A (indicated by dotted lines 20' and 20"). Additionally, tube 25 of one embodiment of the present invention or helix 24 of an alternate embodiment of the present invention, could permit guide wire 30 to rotate freely within the filter (shown by arrows B) without causing blood permeable sac 23 to become wrapped around guide wire 30. Furthermore, suspension strut 22 may absorb minor longitudinal movements of guide wire 30, without causing support hoop 21 to lose apposition to the vessel wall. Thus, transmission of minor longitudinal movements of guide wire 30 to vascular filter 20, e.g., due to catheter exchange, may be mitigated.

Figure 6A:
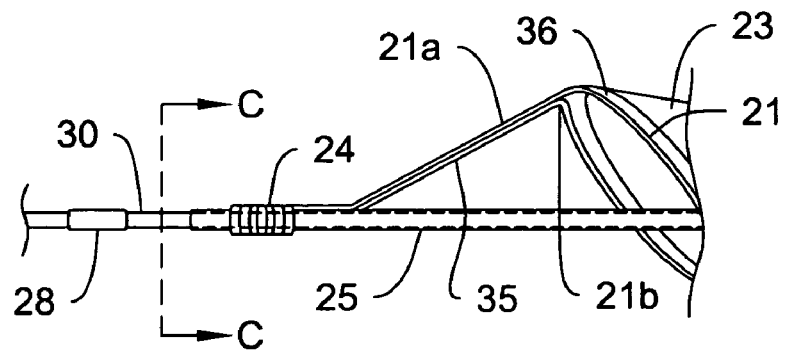

Referring now to FIGS. 6A through 6F, construction details of one embodiment of the present invention are described. In FIG. 6A, details of an embodiment of support hoop 21 and suspension strut 22 are shown. As illustrated, suspension strut 22 may be formed from proximally extending portions 21a and 21b of support hoop 21, and could also include additional support member 35 welded or bonded to portions 21a and 21b. In one embodiment, proximal portions 21a and 21b may be attached to tube 25, for example, by wrapping or entwining proximal portions 21a and 21b to form helix 24 around tube 25. In an alternate embodiment, proximal portions 21a and 21b may be slideably attached to guide wire 30 by wrapping or entwining proximal portions 21a and 21b to form helix 24 around guide wire 30. Helix 24 may be prevented from untwining, for example, by using biocompatible material for welding, crimping, tieing or other bonding method. Stop 28 may consist of a weld bead, length of shrink tube, step in guide wire 30, or similar structure for limiting proximal movement of the filter assembly over guide wire 30.

Turning back to FIG. 3, support hoop 21 could be of a circular or rectangular cross-section. During deployment and retrieval of vascular filter 20, support hoop 21 may fold in half and collapse to fit within the guide wire lumen of a standard balloon catheter. Alternatively, separate delivery and/or retrieval sheath may be employed. When vascular device 20 is in a deployed state, as depicted in FIG. 3, support hoop 21 could resume its pre-formed shape. Support hoop 21 could be made of a bio-compatible super-elastic material, such as a nickel-titanium alloy ("nitinol") wire, a multi-strand nitinol cable, a spring tempered stainless steel, etc.

Support hoop 21 optionally may include any of the articulation regions described in commonly owned U.S. Pat. No. 6,129,739, which is incorporated herein by reference. Thus, for example, support hoop may be a wire of uniform thickness, a wire having one or more reduced thickness regions, a wire having a gradual taper from its proximal ends towards its midpoint, or a pair of spines spanned by a polymer bridge or bridged by the overlapping seam of blood permeable sac 23, as described in the above-incorporated patent.

Sac 23 may be constructed of a thin, flexible biocompatible material, and bonded to support hoop 21 by seam 36 or other suitable means described in the above-incorporated patent. Suitable materials for use in constructing sac 23 include polyethylene, polypropylene, polyurethane, polyester, polyethylene tetraphlalate, nylon, polytetrafluoroethylene, or combinations thereof. The sac material may be sufficiently thin so that the sac is non-thrombogenic, and possibly includes openings or pores that permit blood cells to pass through the sac substantially unhindered, while capturing any larger emboli, thrombus, or foreign bodies that may be released during a procedure, such as angioplasty or stent placement.

Advantageously, the number and distribution of pores could be tailored to the specific application of the vascular filter. Thus, for example, where the filter is to be used in conjunction with angioplasty of saphenous vein grafts, where large quantities of friable plaque are expected to be liberated, larger pores may be used to permit smaller particles to pass through the filter to prevent possible clogging of the pores and blood flow interruption. In contrast, smaller pores may be used in filters intended for carotid angioplasty applications, because less material is expected to be liberated and it may be advantageous to prevent even small particles from reaching the brain.

In one embodiment of the present invention, blood permeable sac 23 may have openings or pores in a range of approximately 20 to 400 microns in diameter. These pore sizes probably will permit blood cells (which have a diameter of approximately 5 to 40 microns) to easily pass through the sac, while capturing thrombi or emboli. Alternate pore densities and sizes may be empirically selected after considering potential trade-offs in efficacy, ease of use, and other related factors that will be apparent to one skilled in the art.

Additionally, the filter membrane may be coated with a lubricious coating that incorporates anti-thrombogenic agents, such as heparin. However, lubricious coating, such as a hydrophobic or hydrophilic thin layer, should not occlude the pores of the filter sac. Advantageously, such lubricious coating may decrease friction between the filter assembly and the delivery sheath, possibly enabling a lower delivery profile for the vascular filter. The anti-thrombogenic agents could reduce the amount of clot that forms on the filter membrane.

In one method of manufacture, pores in blood permeable sac 23 may be formed using a laser drill. In this method, a thin sheet of flexible biocompatible material could be first thermoformed to create sac 23, for example, by stretching the sheet over a mandrel, by dip forming, or by blow molding. Alternatively, sac 23 may be fabricated from an extruded tube of the biocompatible material. A flat metal mask, having holes approximately the size of the desired pores could then be used to shield the sac, and a laser having a beam diameter equal to or greater than the diameter of the mask may illuminate the mask. Laser beam passing through the holes in the mask and striking the sac therein could then form the desired pores. Laser drilling may also be accomplished using a laser having a beam diameter approximately the size of the desired pores, in which case each pore could be drilled individually. Alternatively, sac 23 may be manufactured of a bio-compatible woven material, for example, formed from the above-mentioned polymers, having pore diameters determined as a function of the pattern and tightness of the weave.

Figure 6B:
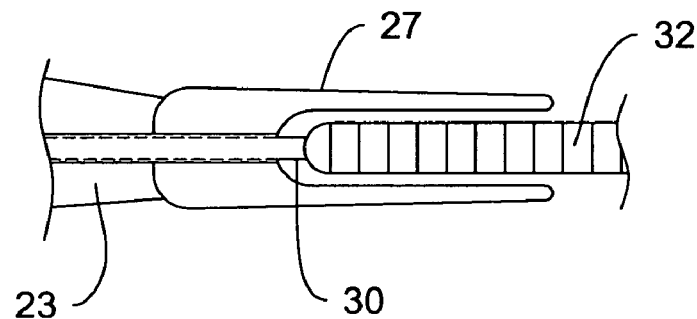

Referring now to FIG. 6B, nose cone 27 may be attached proximate the distal end of blood permeable sac 23, and could include a lumen for containing a portion of floppy tip 32 of guide wire 30 therethrough. This arrangement may shorten the overall exposed length of floppy tip 32, which arrangement could be especially desirable for filters intended for short or very tortuous vessels, such as the renal arteries. While in the illustrations of FIGS. 3-6, blood permeable sac 23 is shown attached at its distal end to nose cone 27, it is to be understood that the distal end of tube 25 may instead be attached to nose cone 27 with the distal end of blood permeable sac 23 also affixed proximate the distal end tube 25.

Figure 6C:
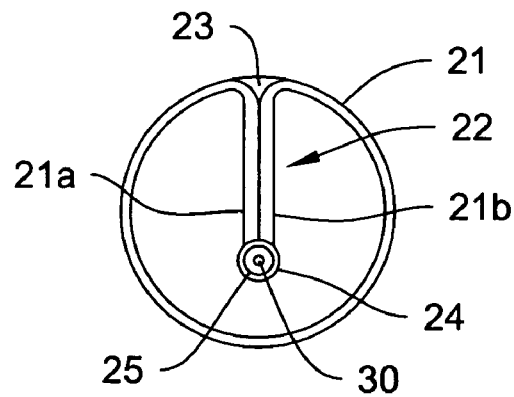
FIG. 6C is a end view of the vascular filter taken along view line C--C of FIG. 6A.

FIG. 6C provides an end view of vascular filter 20 taken along view line C--C of FIG. 6A. Suspension strut 22 probably includes proximally extending portions 21a and 21b of support hoop 21, and additional support member 35 is obscured from view. In one embodiment of the present invention, portions 21a and 21b may be wrapped around tube 25 to from a helical attachment point 24. In an alternate embodiment of the present invention, portions 21a and 21b could be wrapped around guide wire 30 to form, for example, helix 24. Helix 24 may be prevented from untwining, for example, by using biocompatible material for welding, crimping, tieing or other bonding method. When viewed along line C-C as deployed in a vessel, support hoop 21 and blood permeable sac 23 desirably conform to the perimeter of the vessel.

Support hoop 21 is desirably constructed from approximately 0.0035" diameter nitinol wire tapered (by a grinding, chemical etching, or electroless polishing process) to about 0.002" diameter at a point on the support hoop approximately opposite to the point where support hoop 21 transitions into suspension strut 22. Support hoop 21 also may include radiopaque features, such as gold or platinum bands (not shown), spaced at intervals around the circumference of support hoop 21, or a flat or round coil of radiopaque material wrapped around the support hoop, or a gold plated coating.

Figure 6D:
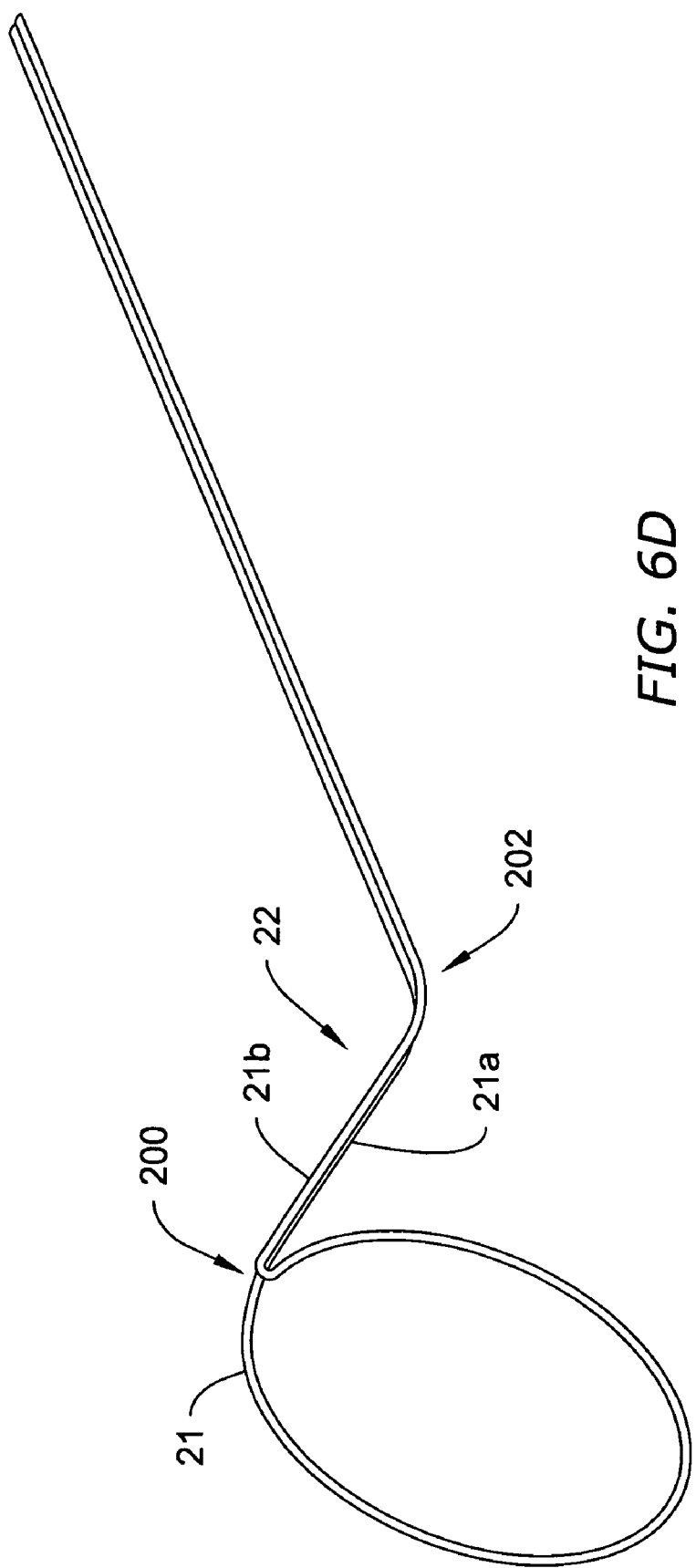
FIGS. 6D-6F are detailed views showing the construction of the filter hoop, the suspension struts, and the helical attachment.
Figure 6E:
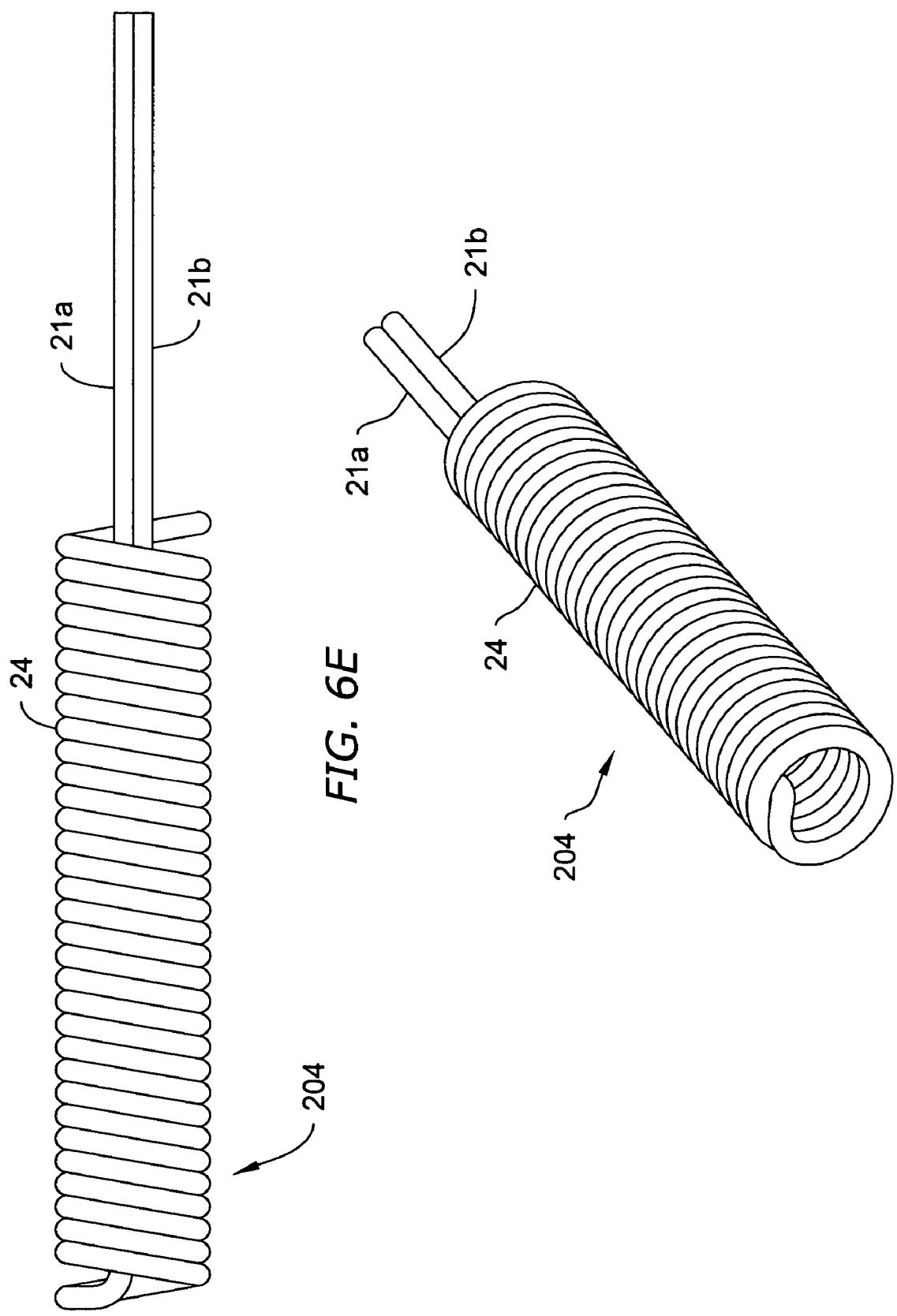
Figure 6F:
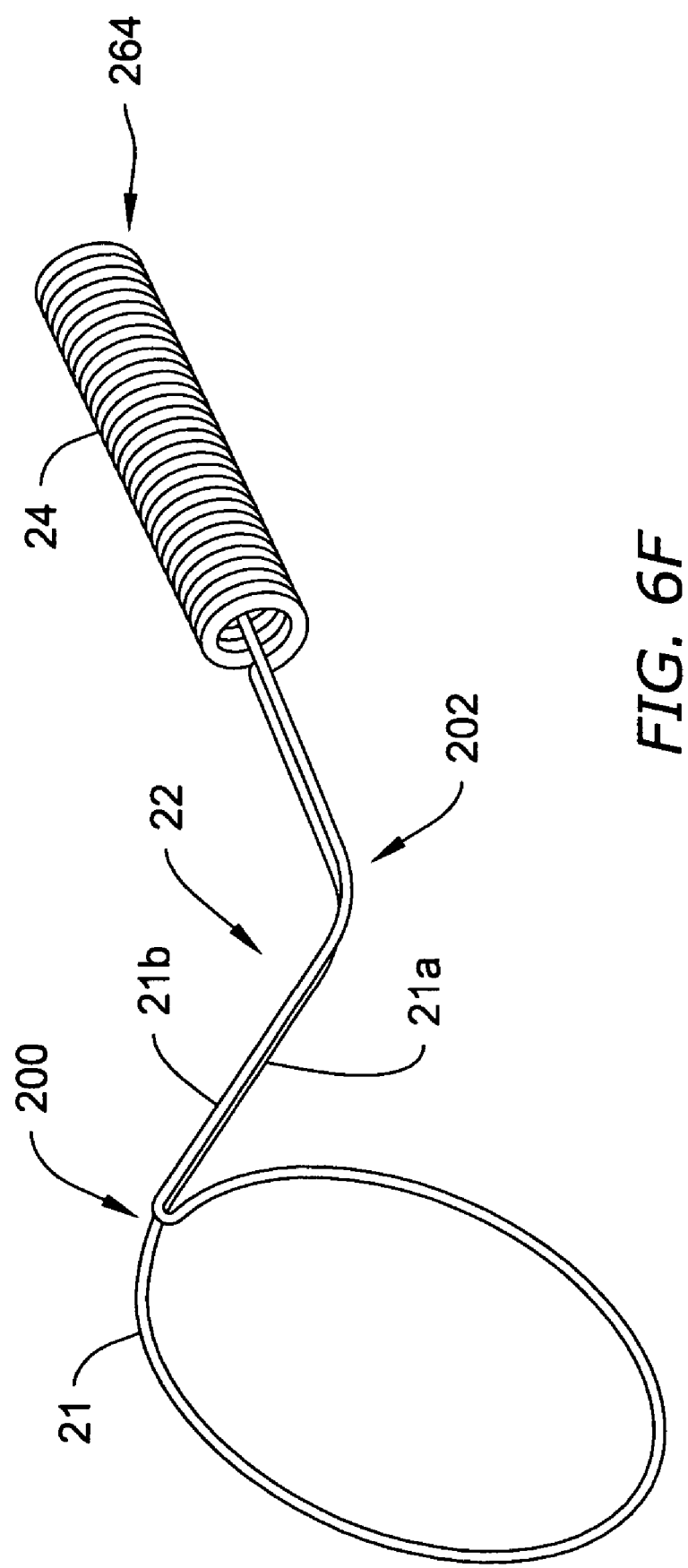

Referring now to FIGS. 6D through 6F, construction details of one embodiment of the present invention are described for attaching suspension strut 22 to tube 25 or around guide wire 30 by wrapping to form helix 24. As illustrated in FIG. 6D, a single continuous strand of wire may be used to form filter support hoop 21 proximate the mid-point of the wire. At location 200 where the two sections of the wire forming filter support hoop 21 join, suspension strut 22 may be formed from proximally extending portions 21a and 21b of filter support hoop 21, and may also include additional support member 35 (see FIG. 6A) welded or bonded to portions 21a and 21b.

In one embodiment, proximal portions 21a and 21b may have a first articulation point 202, and thereafter extend in the proximal direction. After traversing a predetermined distance in the proximal direction, the wire portions 21a and 21b may have a second articulation point 204. As illustrated in FIGS. 6E and 6F, the sections of wires 21a and 21b proximal of articulation point 204 may be wrapped or entwined, in the distal direction, around the section of wires 21a and 21b between articulation points 202 and 204, thereby forming helix 24. It may be desirable for the helix diameter to be sufficiently wide for slideably accommodating tube 25 through the lumen of helix 24. In an alternate embodiment, guide wire 30, instead of tube 25, may pass through the lumen of helix 24.

In another embodiment, sections of wires 21a and 21b may be wrapped or entwined starting from articulation point 202 and extending in the proximal direction to form helix 24. Again, it may be desirable for the helix diameter to be sufficiently wide for slideably accommodating tube 25 through the lumen of helix 24. In an alternate embodiment, guide wire 30, instead of tube 25, may pass through the lumen of helix 24.

Turning now to FIGS. 6G-6P, several alternative embodiments for mechanically coupling suspension strut 22 to guide wire 30 or to tube 25 are illustrated.

Figure 6G:
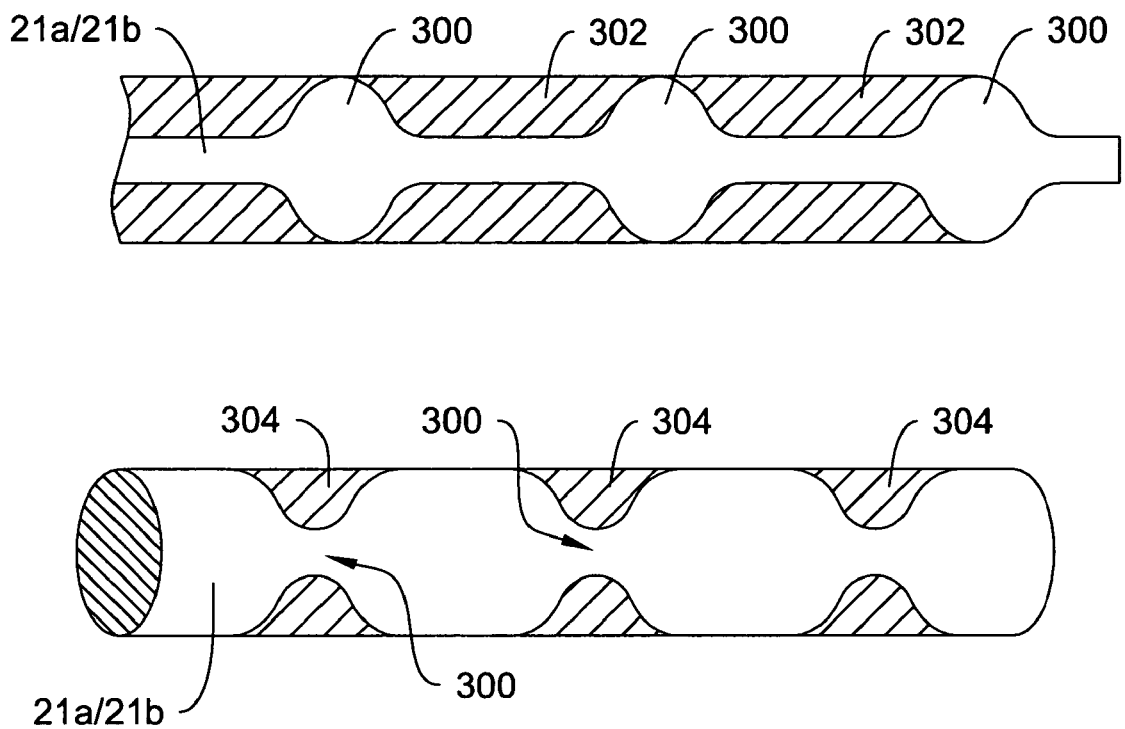
FIGS. 6G-6P illustrate alternate embodiments for attaching the one or more suspension struts to the support tube and/or the guide wire.

FIG. 6G shows one such embodiment wherein one or more sections 300 of wire 21a and/or 21b forming suspension strut 22 may be stamped "flat", thereby forming indentations, proximal of articulation point 202. As such, the one or more "flat" sections 300 on wire 21a and/or 21b may be separated by the normally round sections of wire 21a and/or 21b. Wires 21a and 21b of suspension strut 22 may then be attached to tube 25, for example, by bio-compatible welding, solder, adhesive, etc., for filling indented sections such as 302 and 304.

Figure 6H:
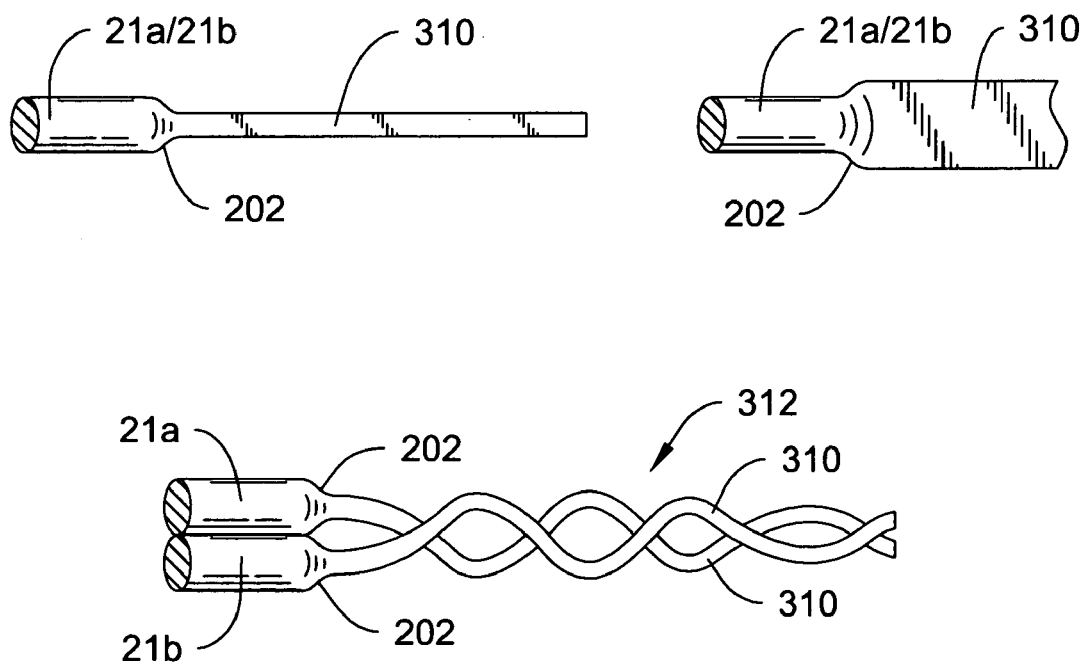

FIG. 6H illustrates another embodiment for mechanically coupling suspension strut 22 to tube 25. In one such implementation, the entire lengths of wires 21a and 21b, proximal of articulation point 202, may be first stamped flat (310). Flattened sections 310 of wires 21a and 21b, proximal of articulation region 202, may then be twisted together (312) and then attached to tube 25, for example, by bio-compatible welding, solder, adhesive, etc. Alternately, the round sections of wires 21a and 21b, proximal of articulation region 202, may be first twisted together, then stamped flat (310), and then attached to tube 25, for example, by bio-compatible welding, solder, adhesive, etc.

Figure 6I:
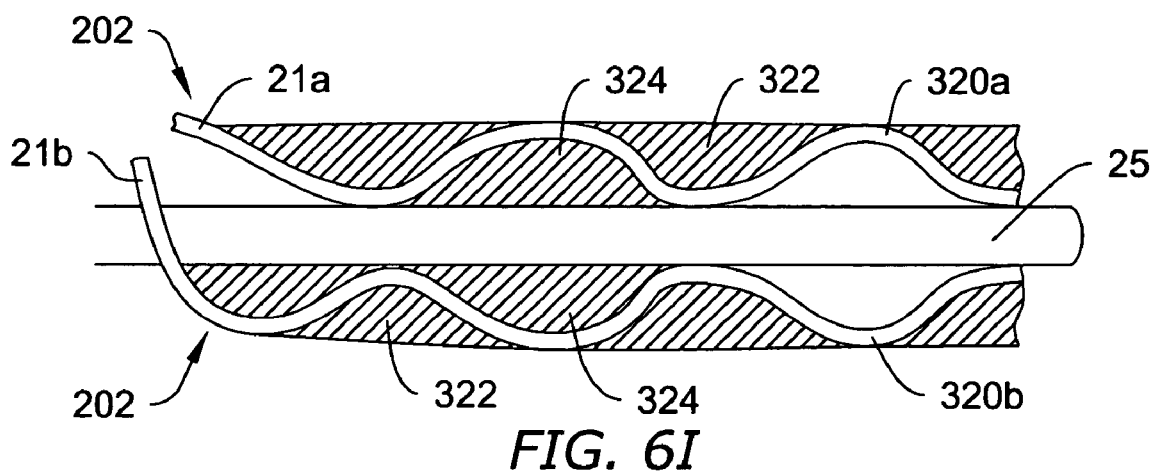

FIG. 6I shows yet another embodiment for mechanically coupling suspension strut 22 to tube 25. As such, the entire lengths of wires 21a and 21b, proximal of articulation point 202, may be formed into zig-zag shape 320a and 320b, respectively, along its length. Zig-zag region 320a of wire 21a and region 320b of wire 21b may then be placed at diametrically opposite locations on the circumference of tube 25, and held in place, for example, by bio-compatible welding, solder, adhesive, etc. As such, the one or more cavities 322 and 324 could get filled with the bio-compatible bonding material.

Figure 6J:
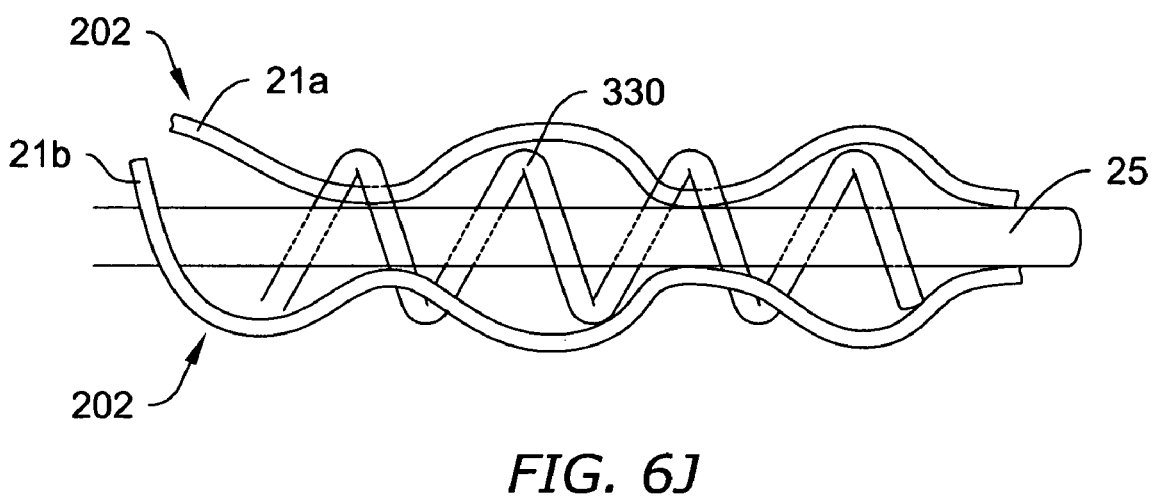

FIG. 6J illustrates another embodiment for mechanically coupling suspension strut 22 to tube 25, wherein the portions of wires 21a and 21b, proximal of articulation point 202, are weaved through coil 330. As shown, coil 330 may be placed around tube 25. Alternately, wires 21a and 21b, proximal of articulation point 202 could be mechanically attached to tube 25 using a separate piece of wire forming a longitudinally extending helix around tube 25 such that the wires of suspension strut 22 may be weaved through alternate turns of the helix forming wire. It may be advantageous to place wires 21a and 21b in diametrically opposite locations and extending proximally along the outside surface of tube 25. Wires 21a and 21b of suspension strut 22, proximal of articulation point 202, may then be held in place, for example, by bio-compatible welding, solder, adhesive, etc.

Figure 6K:
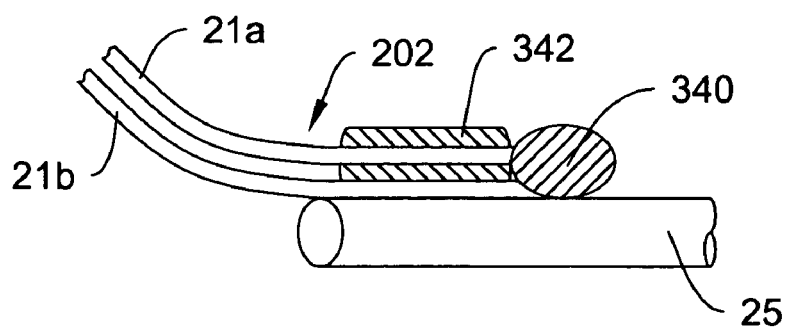

FIG. 6K shows yet another embodiment for mechanically coupling suspension strut 22 to tube 25. As shown, the proximal ends of wires 21a and 21b may be bonded together forming ball 340. Ball 340 may be formed using, for example, bio-compatible welding, solder, adhesive, etc. Sections of wires 21a and 21b, proximal of articulation point 202, may be placed on the outside surface of tube 25, and extended longitudinally in the proximal direction. Wires 21a and 21b of suspension strut 22, proximal of articulation point 202, may then be held in place on tube 25, for example, by bio-compatible welding, solder, adhesive, etc. between articulation point 202 and ball 340.

Figure 6L:
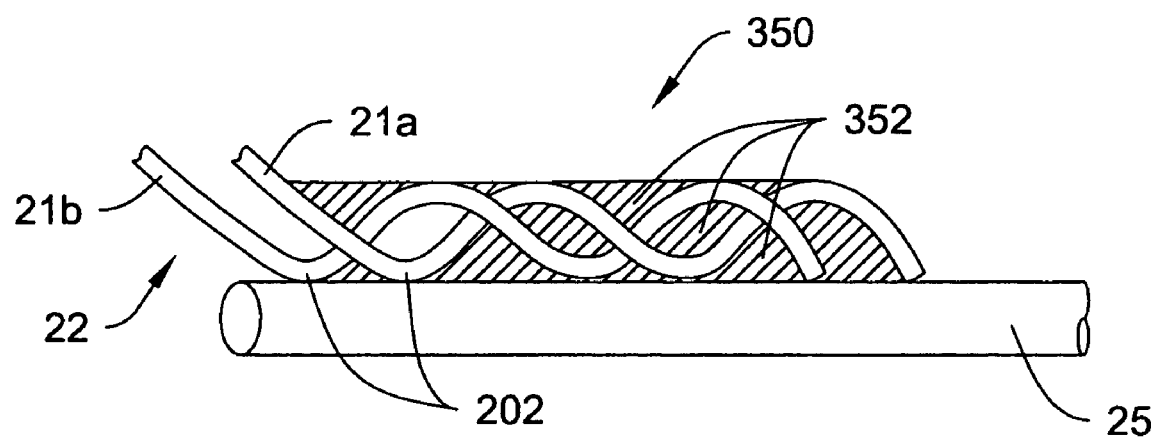

FIG. 6L illustrates yet another embodiment for mechanically coupling suspension strut 22 to tube 25. Wires 21a and 21b, proximal of articulation point 202, may be first twisted together (350), and then may be placed on the outside surface of tube 25, and extended longitudinally in the proximal direction. Wires 21a and 21b of suspension strut 22, proximal of articulation point 202, may then be held in place on tube 25, for example, by bio-compatible welding, solder, adhesive, etc., applied such that spaces between the twisted wires, between the twisted wires and tube 25, etc. get filled (352) with the bio-compatible bonding material.

Figure 6M:
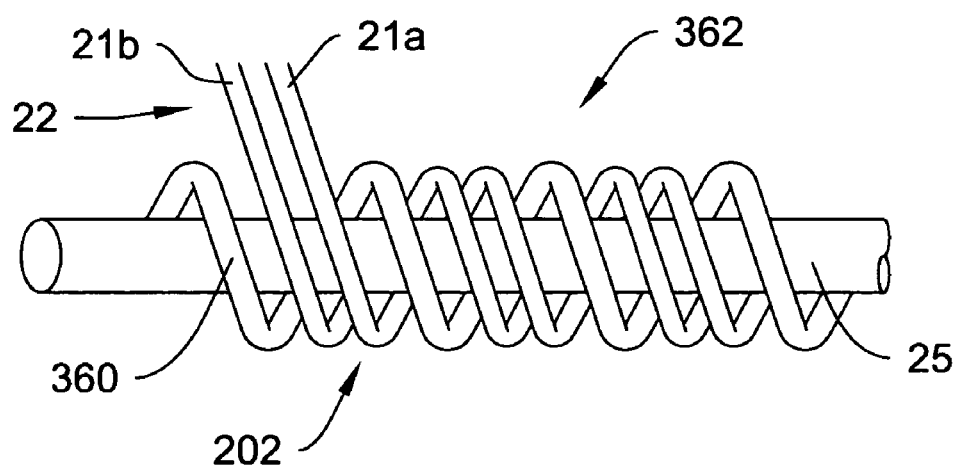

FIG. 6M shows another embodiment for mechanically coupling suspension strut 22 to tube 25. First, base coil 360 may be placed proximal the distal end of tube 25. Next, wires 21a and 21b, proximal of articulation point 202, may be coiled around base coil 360 (362). As such, the mating pitch of base coil 360 and coiled section 362 of suspension strut 22 could be threaded together. The now combined base coil 360 and coiled section 362 of suspension strut 22 may now be held in place on tube 25, for example, by biocompatible welding, solder, adhesive, etc., applied such that spaces between base coil 360, coiled section 362, and tube 25 get filled (not shown) with the bio-compatible bonding material.

For one with ordinary skill in the art, it may be apparent that tube 25 may not be required. The combined base coil 360 and coiled section 362 of suspension strut 22, as described in the foregoing, may be held together, for example, by bio-compatible welding, solder, adhesive, etc., applied such that spaces between base coil 360 and coiled section 362 get filled (not shown) with the bio-compatible bonding material. Guide wire 30 may be passed through the lumen of the combined base coil 360 and coiled section 362 of suspension strut 22.

Figure 6N:
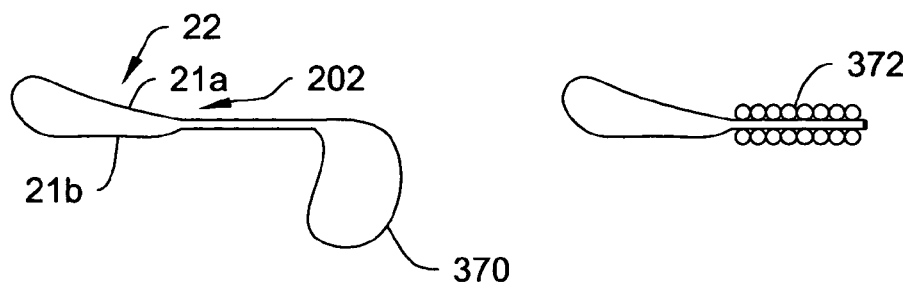

FIG. 6N is another illustration of an alternate embodiment for mechanically coupling suspension strut 22 to guide wire 30 or tube 25. As shown, the proximal ends of wires 21a and 21b of suspension strut 22 are shaped into ring 370, such that the diameter of ring 370 is somewhat larger than the inside diameter of coil 372. The sections of wires 21a and 21b proximal of articulation point 202, and including ring 370, may be placed within the lumen of coil 372. This combination of coil 372 and wires 21a and 21b of suspension strut 22, proximal of articulation point 202, and including ring 370, may be held together, for example, by bio-compatible welding, solder, adhesive, etc. Guide wire 30 may be passed through the lumen of the above described combination. Alternately, tube 25 may be first placed within the lumen of the above described combination, and held together using a bio-compatible bonding material. Guide wire 30 may then pass through the lumen of tube 25.

Figure 6O:
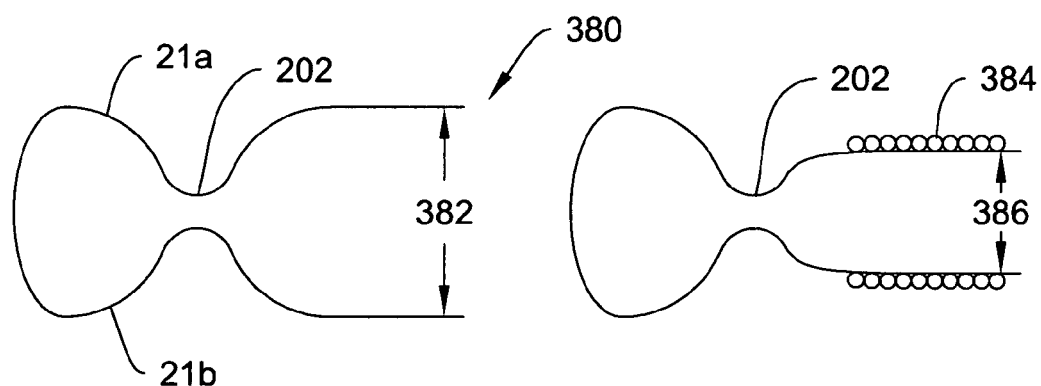

Yet another illustration of an alternate embodiment for mechanically coupling suspension strut 22 to guide wire 30 or tube 25 is illustrated in FIG. 6O. As shown, the ends of wires 21a and 21b of suspension strut 22, proximal of joint articulation point 202, are spread apart distance 382. It may be advantageous for distance 382 to be larger than inside diameter 386 of coil 384. The section of suspension strut 22 proximal of articulation point 202 having distance 382 therebetween may be temporarily squeezed for placement within the lumen of coil 384. Once placed within the lumen of coil 384, the squeezing pressure at the proximal ends of suspension strut 22 may be removed, and the wires permitted to once again spread apart under their elastic force. This combination of coil 384 and wires 21a and 21b of suspension strut 22, proximal of articulation point 202, may be held together, for example, by bio-compatible welding, solder, adhesive, etc. Guide wire 30 may be passed through the lumen of the above described combination. Alternately, tube 25 may be first placed within the lumen of the above described combination, and held together using a bio-compatible bonding material. Guide wire 30 may then pass through the lumen of tube 25.

Figure 6P:
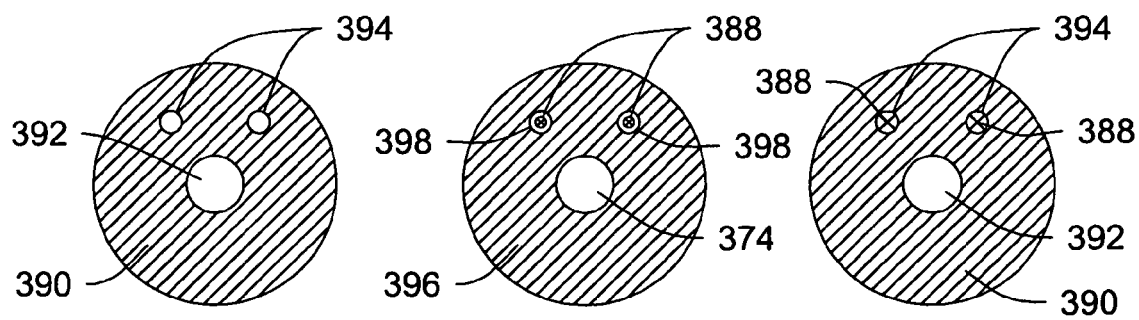

FIG. 6P shows another embodiment for mechanically coupling suspension strut 22 to tube 390. As shown, tube 390 advantageously may be a thick-walled cylindrical element having lumen 392 therethrough, but similar to tube 25 in all other aspects. Two holes 394, having inside diameters somewhat smaller than the outside diameters of wires 21a and 21b, may be drilled into the distal end of tube 390. Tube 390 may then be heated (396) to a temperature higher than the room temperature such that the inside diameters of holes 394 become somewhat larger (398) than the outside diameters of wires 21a and 21b. As a consequence, inside diameter 374 of the lumen through heated tube 396 may also become somewhat bigger than inside diameter 392 through cold tube 390. The proximal ends of wires 21a and 21b (388) each may be inserted into each of holes 398 of heated tube 396. Heated tube 396 may then be cooled to its original room temperature resulting in the diameters of holes 398 decreasing to their original room temperature size 394, and the inside diameter of lumen 374 also decreasing to its original room temperature size 392. Holes 394, having the proximal ends of wires 21a and 21b therein (388), may advantageously provide a substantially tight grip on the proximal ends of wires 21a and 21b such that the proximal ends of suspension strut 22 get "locked in" in tube 390. Guide wire 30 may be passed through lumen 392 of tube 390.

As previously discussed, helix 24 may be prevented from untwining, for example, by using biocompatible material for welding, crimping, tieing, shrink tube, or other bonding method. Additionally, as discussed earlier, a bio-compatible super-elastic material, such as a nickel-titanium alloy ("nitinol") wire, a multi-strand nitinol cable, a spring tempered stainless steel, etc. may be used for filter support hoop 21, suspension strut 22, and helix 24.

In one embodiment of the present invention, vascular filter 20 desirably fits within a delivery sheath having an inner diameter of about 0.033", and could be useable with a delivery sheath having an inner diameter of approximately 0.026". The deployed diameter of support hoop 21 desirably is about 7 mm, while guide wire 30 may have a diameter of approximately 0.014".

Previously known vascular filters typically may require use of a delivery catheter for deploying the filter followed first by insertion and then removal of an interventional device, and then followed by re-insertion of a retrieval catheter for removing the filter. Accordingly, the vascular filter design complying with the embodiments of the present invention desirably permits the filter to be contracted to its delivery and/or retrieval state within the guide wire lumen of previously known conventional interventional devices. Thus, the system of the present invention may reduce the time, effort and trauma accompanying the additional steps of previous designs wherein the use of a delivery and/or retrieval catheter may have been necessary.

It is contemplated that in operation, the vascular filter of the present invention may be deployed in a vessel using a delivery sheath such as described hereinafter. The guide wire to which the vascular filter is attached could then be used to insert an interventional device, e.g., an angioplasty catheter, atherectomy device or stent delivery system, to perform the desired diagnostic or therapeutic procedure. Upon completion of the procedure, the interventional device is desirably advanced to capture the filter, thereby permitting the vascular filter and interventional device to be withdrawn together.

Alternatively, the interventional device may be held stationary, and the guide wire retracted proximally to pull the vascular filter into the guide wire lumen of the interventional device. This latter method of retrieving the vascular filter may be particularly advantageous, because as the filter is dragged along the vessel wall (or through the interior of a stent, if deployed), additional emboli material may be collected from the vessel wall. In this manner, emboli that might not be liberated until full blood flow is restored in the vessel may be collected prior to closure and withdrawal of the vascular filter.

Figure 7A:
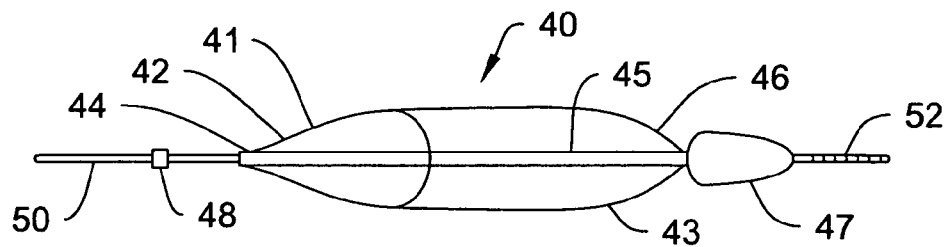
FIGS. 7A-7C are side, top and end views of an alternative embodiment of the vascular filter of the present invention.
Figure 7B:
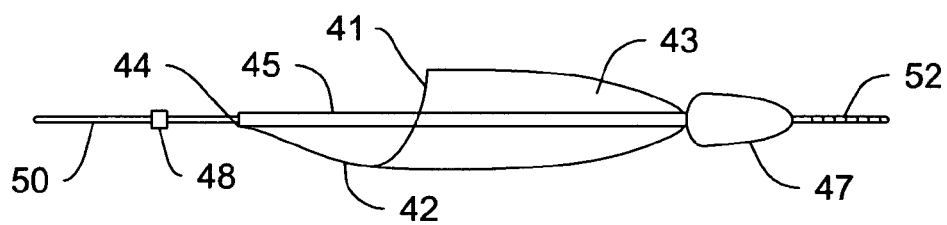
Figure 7C:
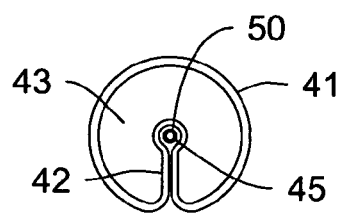

Referring now to FIGS. 7A-7C, an alternative embodiment of the vascular filter of the present invention is described. Vascular filter 40 is similar in construction to filter 20 of FIGS. 3-6, and includes support hoop 41, suspension strut 42, sac 43, fixation point 44, tube 45 and nose cone 47. Tube 45 is desirably mounted for rotational and axial movement around guide wire 50 between proximal stop 48 and floppy tip 52. Alternately, the ends of suspension strut 42 could be entwined around guide wire 50, thereby forming a helix 44, and distal end 46 of blood permeable sac 43 may be mounted to nose cone 47, which in turn may contain guide wire 30 in a lumen therethrough. Helix 44 may be prevented from untwining, for example, by using biocompatible material for welding, crimping, tieing or other bonding method. In this alternate embodiment, tube 45 is not required, and helix 44 having guide wire 50 passing therethrough, could permit guide wire 50 to move independently of filter 40. Filter 40 is desirably constructed in the manner and with the materials described hereinabove.

The one aspect in which filter 40 differs from filter 20, described hereinabove, is that suspension strut 42 is gradually curved. As in the aforementioned embodiments of FIGS. 3-6, support hoop 41 appears elliptical when viewed in profile, and desirably includes one or more suspension strut 42 that permits filter sac 43 to become eccentrically displaced from guide wire 50 without losing proper apposition to the vessel wall.

Figure 8A:
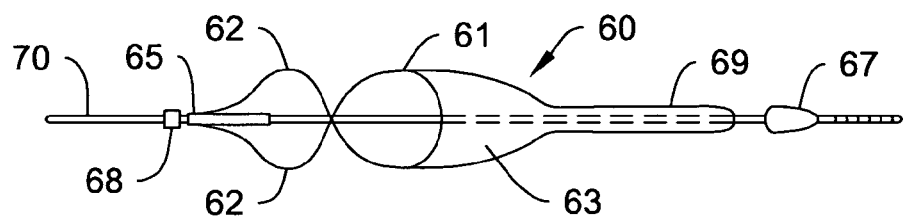
FIGS. 8A and 8B are side and top views of another alternative embodiment of the present invention.
Figure 8B:
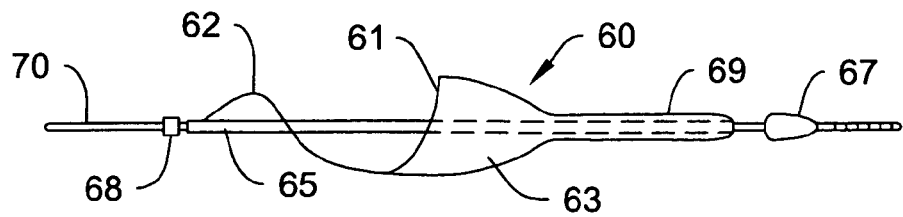

With respect to FIGS. 8A and 8B, another alternative embodiment of the vascular filter of the present invention is described. Vascular filter 60, shown in a deployed state, may have support hoop 61 coupled to a multi-turn helical suspension strut 62. Suspension strut 62 may include one or more side turns 69 that join support hoop 61, and additionally suspension strut 62 could be coupled to tube 65 mounted on guide wire 70 between proximal stop 68 and nose cone 67. Nose cone 67 may be affixed to guide wire 70 distal of tube 65. The proximal end of blood permeable sac 63 is desirably affixed to support hoop 61, while the distal end may be affixed directly to tube 65.

Alternatively, the ends of suspension strut 62 could be entwined around guide wire 70, thereby forming a helix, and the distal end of blood permeable sac 63 may be mounted to nose cone 67, which in turn may contain guide wire 70 in a lumen therethrough. The helix around guide wire 70 formed by suspension strut 62 may be prevented from untwining, for example, by using biocompatible material for welding, crimping, tieing or other bonding method. In this alternate embodiment, tube 65 is not required, and the helix having guide wire 70 passing therethrough, could permit guide wire 70 to move independently of filter 60.

Blood permeable sac 63 could include a tapered distal portion which desirably reduces the risk of bunching during retrieval. In accordance with this embodiment of the present invention, vascular filter 60 may be contractable to a small profile delivery state. When deployed from a delivery catheter, side turns 69 desirably expand to contact the walls of the vessel proximate the location at which support hoop 61 contacts the vessel wall. Side turns 69 of suspension strut 62 are expected to stabilize support hoop 61 and sac 63 when vascular filter 60 is deployed within a blood vessel. Additionally, side turns 69 may facilitate eccentric displacement of support hoop 61 and sac 63 relative to the longitudinal axis of a vessel. Accordingly, side turns 69 of suspension strut 62 desirably enhance apposition of the filter against the vessel wall, potentially enhancing the safety and reliability of the device.

Figure 9:
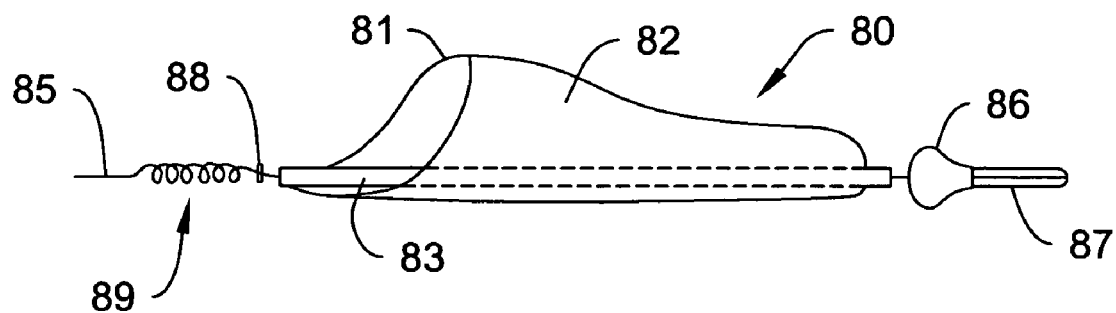
FIG. 9 is a side view of a further alternative embodiment of a vascular filter of the present invention in a deployed state.
Figure 10:
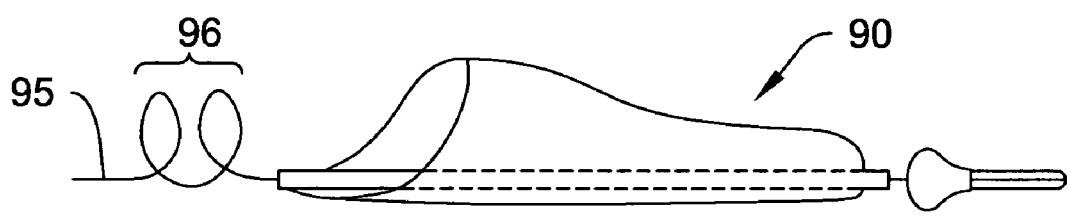
FIG. 10 is a side view of a yet another alternative embodiment of a vascular filter of the present invention in a deployed state.

Referring now to FIGS. 9 and 10, additional alternative embodiments of the vascular filter of the present invention are described. As illustrated in FIG. 9, vascular filter 80 may consist support hoop 81 and tapered blood permeable sac 82 mounted on tube 83. Support hoop 81 is desirably coupled directly to the proximal end of tube 83. Filter 80 may be captured on guide wire 85 between nose cone 86, which could be affixed to guide wire 85 just proximal of floppy tip 87, and proximal stop 88. As previously described, additional embodiments without tube 83 are also possible.

In one embodiment of the present invention, guide wire 85 may include articulation region 89 having a series of small diameter coil turns. Articulation region 89 could act as a bend point in the guide wire, possibly permitting better conformance of the guide wire to tortuous anatomy and desirably improving capture efficiency in tortuous vessels, such as illustrated in FIG. 2. Articulation region 89 may provide an alternative configuration for permitting the vascular filter to become eccentrically displaced relative to the axis of guide wire 85.

FIG. 10 depicts an alternative configuration of the vascular filter of FIG. 9, in which filter 90 is essentially constructed in the same manner as filter 80. In this embodiment, however, guide wire 95 is shown having articulation region 96 with two or more large diameter coils. In addition to providing a region that permits articulation of the filter relative to the axis of guide wire 95, the large diameter coils of the articulation region 96 may also assist in stabilizing the filter within the vessel after deployment.

Figure 11:
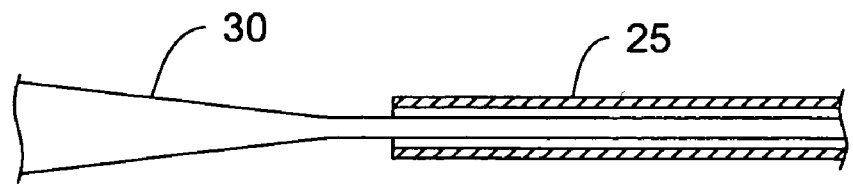
FIG. 11 is detailed view of a tapered guide wire and support tube arrangement suitable for use in the present invention.

Referring now to FIG. 11, an additional feature that may be advantageously incorporated in the embodiments of the vascular filters of the present invention is described. FIG. 11 depicts an alternative configuration for the junction between a guide wire and the tube on which the filter is mounted. For example, the guide wire in FIG. 11 may be guide wire 30 of the embodiment of FIG. 3, and the tube may represent tube 25 of that embodiment. In accordance with this aspect of the present invention, guide wire 30 is tapered as shown (or includes a step, not shown) to accept tube 25. Consequently, the outer diameter of tube 25 may be made approximately the same as the guide wire thickness itself.

Because the delivery profile of the vascular filter is determined in part by the cumulative thicknesses of the components that lie adjacent to one another in the delivery sheath, use of a tapered or stepped distal region of the guide wire to accept tube 25 may enable the manufacture of significantly smaller profile devices than heretofore available. For example, in an umbrella-type filter, the delivery profile is limited by the need to have multiple suspension strut disposed about the guide wire, and accounts for the difficulty that has been encountered in the field in constructing such filters having small delivery profiles. By comparison, a filter of the type described hereinabove, when collapsed to its delivery profiled, and using the feature illustrated in FIG. 11, may not need to be much larger than the diameter of the guide wire itself.

Figure 12A:
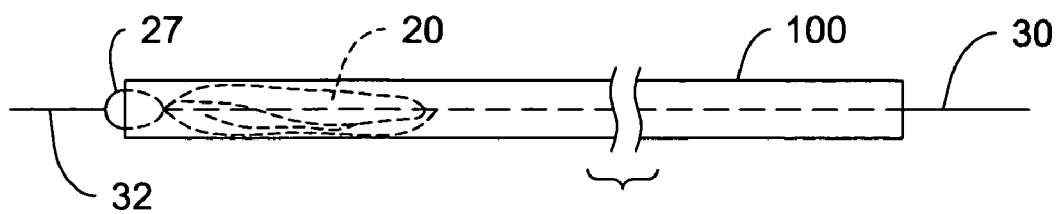
FIGS. 12A-12C are side views illustrating deployment of the vascular filter of the present invention using a single use splitable delivery sheath.
Figure 12B:
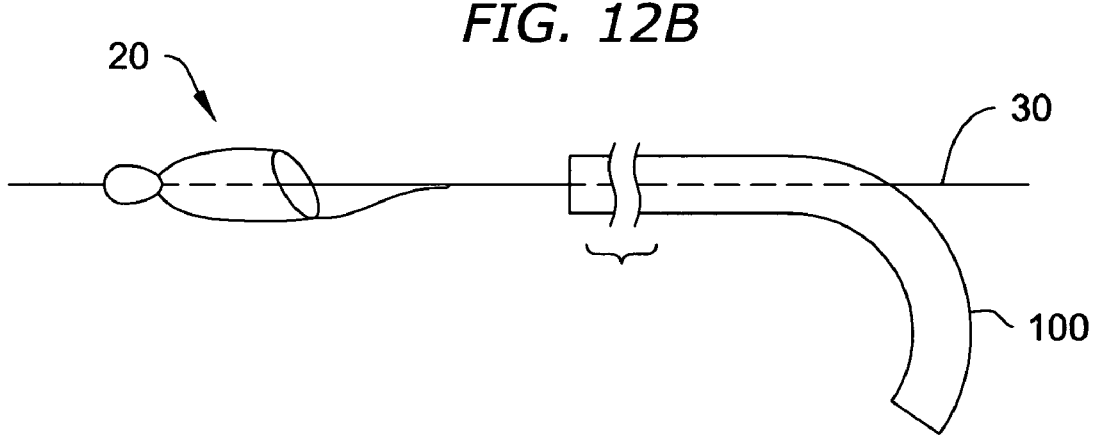
Figure 12C:
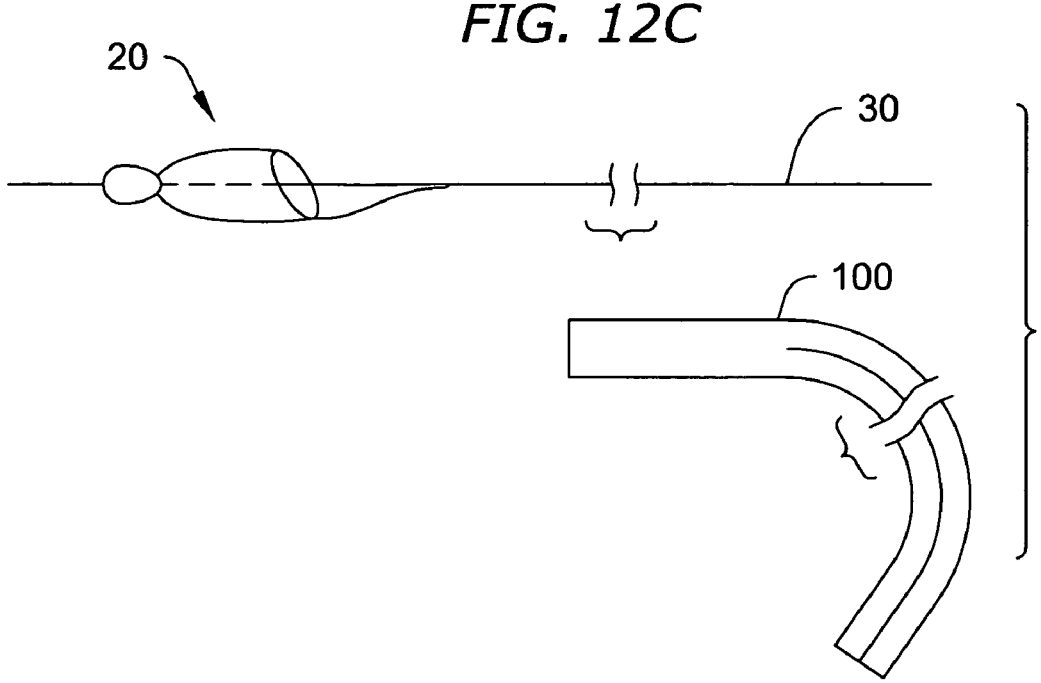

Referring now to FIGS. 12A-12C, a single-use delivery sheath suitable for use with the vascular filter of the present invention is described. In accordance with this aspect of the present invention, guide wire 30 may be of a length suitable for use with rapid-exchange interventional devices. Vascular filter 20 could be disposed in delivery sheath 100 in its contracted configuration, with the proximal end of guide wire 30 extending from the proximal end of sheath 100, and nose cone 27 and floppy tip 32 extending from the distal end of sheath 100, as shown in FIG. 12A. Delivery sheath 100 may be of a soft, flexible biocompatible material, such as polyethylene or other materials typically used in catheter construction.

In accordance with known techniques, the distal region of guide wire 30 and vascular filter may be percutaneously and transluminally inserted into a patient until the vascular filter is at a desired deployment site, as determined, for example, by fluoroscopy. Delivery sheath 100 could then be split, either using a suitable cutting device or along a perforation seam, and retracted proximally with the clinician holding the proximal end of guide wire 30 in one hand, and thereby deploying vascular filter 20 within the vessel, as shown in FIG. 12B, and thus fully removing the delivery sheath from guide wire 30, as shown in FIG. 12C.

Guide wire 30 may thereafter be used in a conventional rapid exchange manner for passing interventional devices, such as atherectomy devices, angioplasty device, and stent delivery systems, to desired locations in the vessel proximal to the location of vascular filter 20. Once the intended diagnostic or therapeutic treatment is performed, guide wire 30 could be withdrawn proximally until the support hoop is drawn into the guide wire lumen of the interventional device, thereby closing the mouth of the filter and preventing emboli collected during the procedure from escaping into the patient's blood stream.

The vascular filter system, when used with delivery sheath 100, may eliminate the need for inserting a separate retrieval catheter to recover the filter. In addition, single-use delivery sheath 100 may discourage off-label repeat use of the vascular filter such as could occur if a separate delivery and retrieval sheath were used, because delivery sheath 100 probably becomes non-reusable once the filter has been deployed. Further still, because delivery sheath 100 need not be capable of transmitting pushing forces, the walls of the sheath may be made very thin.

Figure 13A:
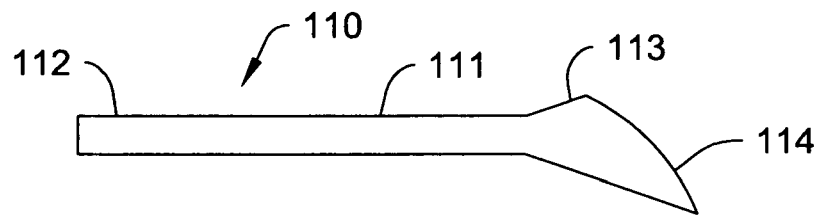
FIGS. 13A and 13B are, respectively, side and top views of an introducer sheath suitable for use with the vascular filter of the present invention.
Figure 13B:
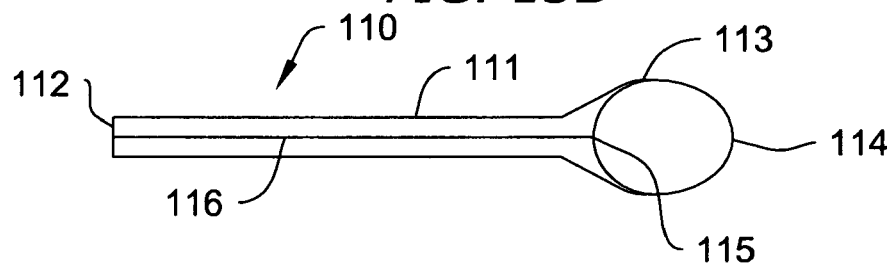

Referring now to FIGS. 13 and 14, introducer sheath 110 and methods of using that sheath in conjunction with vascular filter 20 and delivery sheath 100 of the present invention are described. Introducer sheath 110 may be designed to pass floppy tip 32 of guide wire 30 through the rotating hemostatic valve of a guide catheter without kinking or tangling the floppy tip in the valve. Introducer sheath 110 may be tubular body 111 having distal end 112, funnel-shaped proximal end 113, pull tab 114, central lumen 115 and full-length slit 116, and possibly made from polyethylene, nylon or similar material, having sufficient rigidity to be pushed through a rotating hemostatic valve.

Figure 14A:
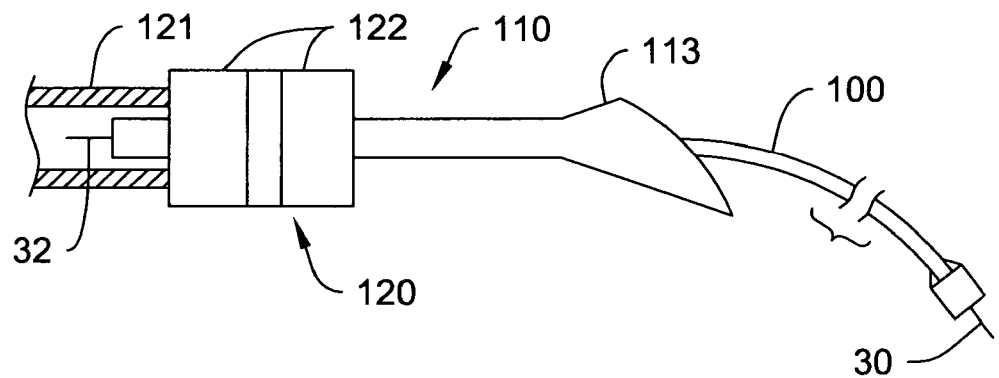
FIGS. 14A and 14B are side views, partially in section, illustrating use of the introducer sheath of FIG. 13 in crossing a rotating hemostatic valve.
Figure 14B:
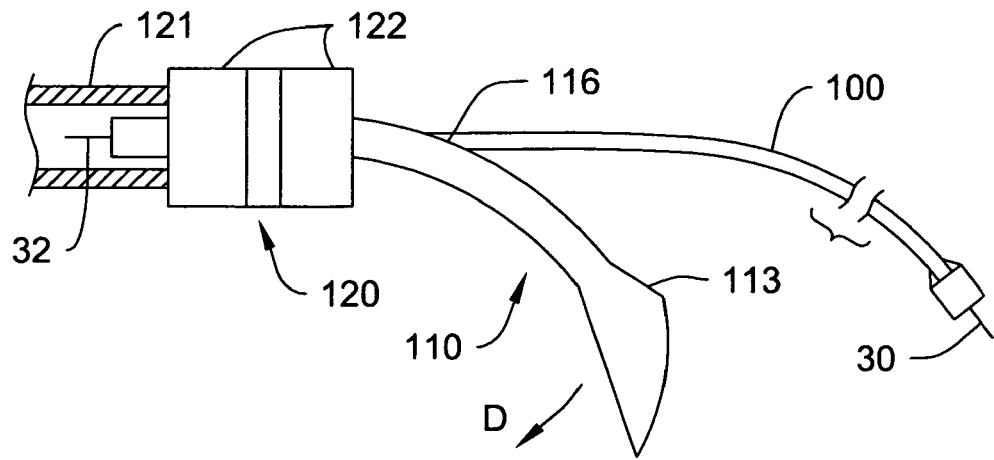

In one method of use, illustrated in FIGS. 14A and 14B, introducer sheath 110 may be advanced through rotating hemostatic valve 120 of guide catheter 121. As will of course be understood by one skilled in the art, guide catheter 121 may be a conventional multi-port guide catheter and could include a membrane that is selectively opened and sealed by rotating nuts 122 of the valve. Delivery sheath 100, which encloses vascular filter 20 and guide wire 30, then may be inserted into funnel-shaped end 113 of the introducer sheath, and advanced to a location at which floppy tip 32 extends into guide catheter 121 distal to valve 120, as depicted in FIG. 14A.

Referring to FIG. 14B, pull tab 114 of introducer sheath 110 may be pulled lo downward in the direction shown by arrow D so that delivery sheath 100 could pass through slit 116 of the introducer sheath. Introducer sheath 110 may be retracted proximally and peeled away from delivery sheath 100 as shown in FIG. 14B until the introducer sheath is entirely removed. Delivery sheath 100, vascular filter 20 and guide wire 30 could then be advanced to the desired location in the vessel, and delivery sheath 100 may be removed to deploy the vascular filter as described hereinabove with respect to FIGS. 12A-12C.

Introducer sheath 110 may permit floppy tip 32 of guide wire 30 to be easily inserted through rotating hemostatic valve 120 of guide catheter 120. The peel-away operation of introducer sheath 110 could facilitate rapid insertion of the vascular filter and guide wire into the guide catheter with minimal effort. Additionally, slit 116 of introducer sheath 110 could prevent destruction of the sheath after the single use, thus possibly enabling the introducer sheath to be used to reintroduce the vascular filter in the same procedure. This may occur, for example, where the clinician begins inserting the vascular filter, but then needs to remove the filter and redirect the floppy tip during the same procedure.

Although illustrative embodiments of the present invention are described above, it will be evident to one skilled in the art that various changes and modifications may be made without departing from the described invention. It is intended in the appended claims to cover all such changes and modifications that fall within the true spirit and scope of the invention.

We claim:

1. An embolic filter assembly, said filter assembly comprising:
    at least one strand of wire forming a support hoop;
    the strand of wire extending from said support hoop and forming at least one suspension strut;
    the suspension strut coupled, at least in part, to a guide wire or a filter wire; and
    a blood permeable sac having an opening, said opening fixedly attached to the support hoop, thereby forming a proximal opening or mouth of the embolic filter;
    wherein the at least one suspension strut is at least in part, entwined around said guide wire or said filter wire, thereby forming a helix around the guidewire or filter wire;
    and wherein the helix is formed by first longitudinally traversing the at least one suspension strut, at least in part, along said guide wire or said filter wire in a distal to proximal direction, and then entwining the at least one suspension strut, at least in part, in the proximal to distal direction.

2. The filter assembly of claim 1, wherein the support hoop is self-expanding.

3. The filter assembly of claim 2, wherein said support hoop has a preformed shape.

4. The filter assembly of claim 1, wherein the support hoop and/or the suspension strut is comprised of a bio-compatible material.

5. The filter assembly of claim 4, wherein the bio-compatible material comprises a nickel-titanium alloy (nitinol).

6. The filter assembly of claim 4, wherein the bio-compatible material comprises stainless steel.

7. The filter assembly of claim 1, wherein the helix defines a lumen, the guide wire or the filter wire moveably passing through the lumen comprised by said helix.

8. The filter assembly of claim 1, wherein the helix is formed by entwining the at least one suspension strut, at least in part, in the distal to proximal direction.

9. The filter assembly of claim 1, wherein the helix is held together with a thread or a wire or a ribbon comprised of a bio-compatible material.

10. The filter assembly of claim 9, wherein the bio-compatible material comprises a nickel-titanium alloy (nitinol).

11. The filter assembly of claim 9, wherein the bio-compatible material comprises stainless steel.

12. The filter assembly of claim 1, wherein the helix is covered with a bio-compatible material.

13. The filter assembly of claim 12, wherein the biocompatible material is a heat shrink tubing.

14. The filter assembly of claim 12, wherein the biocompatible material is an adhesive.

15. The filter assembly of claim 12, wherein the biocompatible material is a soldering material.

16. The filter assembly of claim 12, wherein the biocompatible material is a welding material.

17. The filter assembly of claim 1, wherein emboli-laden blood enters the proximal mouth or opening of the embolic filter, and the emboli becomes entrapped within said blood permeable sac.

18. The filter assembly of claim 1, wherein the at least one suspension strut is comprised of at least two sections of the strand of wire forming the support hoop.

19. The filter assembly of claim 18, wherein the at least one suspension strut has an articulation point whereafter the at least two sections of the strand of wire extend proximally for attachment to a guide wire or a filter wire.

20. The filter assembly of claim 19, wherein the at least two sections of the strand of wire proximal of the articulation point are entwined around the guide wire or the filter wire, thereby forming the helix having the guide wire or the filter wire moveably passing through the lumen comprised by said helix.

21. The filter assembly of claim 19, wherein:
one or more regions on the at least two sections of the strand of wire proximal of the articulation point are stamped flat having one or more regions of unstamped wire therebetween;
the at least two sections of the strand of wire are intertwined and held in place by a bio-compatible bonding material forming a bonded strand of wire; and
the bonded strand of wire is entwined around the guide wire or the filter wire, thereby forming the helix having the guide wire or the filter wire moveably passing through the lumen comprised by said helix.

22. The filter assembly of claim 19, wherein:
the at least two sections of the strand of wire proximal of the articulation point are intertwined together;
one or more regions on the intertwined wire proximal of the articulation point are stamped flat having one or more regions of unstamped wire therebetween;
the intertwined wire is held in place by a bio-compatible bonding material forming a bonded strand of wire; and
the bonded strand of wire is entwined around the guide wire or the filter wire, thereby forming the helix having the guide wire or the filter wire moveably passing through the lumen comprised by said helix.

23. The filter assembly of claim 19, wherein:
the at least two sections of the strand of wire proximal of the articulation point are stamped flat;
the at least two sections of the flattened strand of wire are intertwined and held in place by a bio-compatible bonding material forming a bonded strand of wire; and
the bonded strand of wire is entwined around the guide wire or the filter wire, thereby forming the helix having the guide wire or the filter wire moveably passing through the lumen comprised by said helix.

24. The filter assembly of claim 19, wherein the at least two sections of the strand of wire proximal of the articulation point are weaved through one or more turns of wire forming a coil, and having the guide wire or the filter wire moveably passing through the lumen of the coil.

25. An embolic filter assembly, said filter assembly comprising:
at least one strand of wire forming a support hoop;
the strand of wire extending from said support hoop and forming at least one suspension strut including at least two sections of the strand of wire proximal of an articulation point;
a coil extending over a portion of a guide wire or a filter wire, the coil having an inside diameter defining a lumen;
the suspension strut coupled, at least in part, to the guide wire or the filter wire, such that at least a portion of the at least two sections of the strand of wire proximal of the articulation point extend through the lumen of the coil; and
a blood permeable sac having an opening, said opening fixedly attached to the support hoop, thereby forming a proximal opening or mouth of the embolic filter.

26. The filter assembly of claim 25, wherein the at least two sections of the strand of wire proximal of the articulation point are mechanically attached to the coil by weaving the strand of wire through alternate turns of the coil, and having the guide wire or the filter wire moveably passing through the lumen of the coil.

27. The filter assembly of claim 25, wherein:
the at least two sections of the strand of wire proximal of the articulation point are coiled around the coil;
the coiled strand of wire is bonded to the coil using a bio-compatible bonding material; and
the guide wire or the filter wire moveably passes through the lumen of the coil.

28. The filter assembly of claim 25, wherein:
the at least two sections of the strand of wire proximal of the articulation point are formed into a ring having a diameter greater than the inside diameter of the coil;
the ring squeezed into a smaller diameter and placed within the lumen of the coil and held in place by mechanical forces imposed by the ring onto the inside surface of the coil; and
the guide wire or the filter wire moveably passes through the lumen of the coil.

29. The filter assembly of claim 25, wherein:
the at least two sections of the strand of wire proximal of the articulation point are separated from each other such that the distance between the at least two sections of the strand of wire is greater than the inside diameter of the coil;
the separated proximal sections of the strand of wire squeezed together and placed within the lumen of the coil and held in place by mechanical forces imposed by the at least two sections of the strand of wire onto the inside surface of the coil; and
the guide wire or the filter wire moveably passes through the lumen of the coil.

30. An embolic filter assembly, said filter assembly comprising:
at least one strand of wire forming a support hoop;
the strand of wire extending from said support hoop and forming at least one suspension strut;
the suspension strut fixedly attached, at least in part, to a tube having a moveable guide wire or a moveable filter wire therethrough; and
a blood permeable sac having an opening, said opening fixedly attached to the support hoop, thereby forming a proximal opening or mouth of the embolic filter;
wherein the at least one suspension strut is, at least in part, entwined around said tube, thereby forming a helix around the tube.

31. The filter assembly of claim 30, wherein the helix is formed by entwining the at least one suspension strut, at least in part, in the distal to proximal direction.

32. The filter assembly of claim 30, wherein the helix is formed by first longitudinally traversing the at least one suspension strut, at least in part, along said guide wire or said filter wire in a distal to proximal direction, and then entwining the at least one suspension strut, at least in part, in the proximal to distal direction.

33. The filter assembly of claim 30, wherein the helix is held together with a thread or a wire or a ribbon comprised of a bio-compatible bonding material.

34. The filter assembly of claim 30, wherein the helix is covered with a bio-compatible bonding material.

35. The filter assembly of claim 34, wherein the bio-compatible bonding material is a heat shrink tubing.

36. The filter assembly of claim 34, wherein the bio-compatible bonding material is an adhesive.

37. The filter assembly of claim 34, wherein the bio-compatible bonding material is a soldering material.

38. The filter assembly of claim 34, wherein the bio-compatible bonding material is a welding material.

39. The filter assembly of claim 30, wherein emboli-laden blood enters the proximal mouth or opening of the embolic filter, and the emboli becomes entrapped within said blood permeable sac.

40. The filter assembly of claim 30, wherein the at least one suspension strut is comprised of at least two sections of the strand of wire forming the support hoop.

41. The filter assembly of claim 40, wherein the at least one suspension strut has an articulation point whereafter the at least two sections of the strand of wire extend proximally for attachment to the tube.

42. The filter assembly of claim 41, wherein the at least two sections of the strand of wire proximal of the articulation point are held in place by a bio-compatible bonding material.

43. The filter assembly of claim 41, wherein:
one or more regions on the at least two sections of the strand of wire proximal of the articulation point are stamped flat having one or more regions of unstamped wire therebetween;
the at least two sections of the strand of wire are intertwined and held in place by a bio-compatible bonding material forming a bonded strand of wire; and
the bonded strand of wire is entwined around the tube and held in place by a bio-compatible bonding material.

44. The filter assembly of claim 41, wherein:
the at least two sections of the strand of wire proximal of the articulation point are intertwined together;
one or more regions on the intertwined wire proximal of the articulation point are stamped flat having one or more regions of unstamped wire therebetween;
the intertwined wire is held in place by a bio-compatible bonding material forming a bonded strand of wire; and
the bonded strand of wire positioned on the tube and held in place by a bio-compatible bonding material.

45. The filter assembly of claim 41, wherein:
the at least two sections of the strand of wire proximal of the articulation point are stamped flat;
the at least two sections of the flattened strand of wire are intertwined and held in place by a bio-compatible bonding material forming a bonded strand of wire; and
the bonded strand of wire is entwined around the tube and held in place by a bio-compatible bonding material.

46. The filter assembly of claim 41, wherein the at least two sections of the strand of wire proximal of the articulation point are weaved through one or more turns of wire forming a coil around the tube and held in place by a bio-compatible bonding material.

47. An embolic filter assembly, said filter assembly comprising:
at least one strand of wire forming a support hoop;
the strand of wire extending from said support hoop and forming at least one suspension strut including at least two sections of the strand of wire proximal of an articulation point;
a coil extending over a portion of a tube, the coil having an inside diameter defining a lumen;
the suspension strut fixedly attached, at least in part, to the tube, such that at least a portion of the at least two sections of the strand of wire proximal of the articulation point extends through the lumen of the coil; and
a blood permeable sac having an opening, said opening fixedly attached to the support hoop, thereby forming a proximal opening or mouth of the embolic filter.

48. The filter assembly of claim 47, wherein the at least two sections of the strand of wire proximal of the articulation point are mechanically attached to the coil by weaving the strand of wire through alternate turns of the coil forming wire around the tube and held in place by a bio-compatible bonding material.

49. The filter assembly of claim 47, wherein:
the at least two sections of the strand of wire proximal of the articulation point are coiled around the coil;
the coiled strand of wire is bonded to the coil using a bio-compatible bonding material; and
the tube placed within the lumen of the coil and held in place by a bio-compatible bonding material.

50. The filter assembly of claim 47, wherein:
the at least two sections of the strand of wire proximal of the articulation point are formed into a ring having a diameter greater than the inside diameter of the coil;
the ring squeezed into a smaller diameter and placed within the lumen of the coil and held in place by mechanical forces imposed by the ring onto the inside surface of the coil; and
the tube placed within the lumen of the coil and held in place by a bio-compatible bonding material.

51. The filter assembly of claim 47, wherein:
the at least two sections of the strand of wire proximal of the articulation point are separated from each other such that the distance between the at least two sections of the strand of wire is greater than the inside diameter of the coil;
the separated proximal sections of the strand of wire squeezed together and placed within the lumen of the coil and held in place by mechanical forces imposed by the at least two sections of the strand of wire onto the inside surface of the coil; and
the tube placed within the lumen of the coil and held in place by a bio-compatible bonding material.

52. An embolic filter assembly, said filter assembly comprising:
at least one strand of wire forming a support hoop;
the strand of wire extending from said support hoop and forming at least one suspension strut including at least two sections of the strand of wire proximal of an articulation point;
the suspension strut fixedly attached, at least in part, to a tube having a moveable guide wire or a moveable filter wire therethrough; and a blood permeable sac having an opening, said opening fixedly attached to the support hoop, thereby forming a proximal opening or mouth of the embolic filter;

wherein the at least two sections of the strand of wire proximal of the articulation point are formed into a zig-zag shape;

the zig-zag strand of wire placed on the outside surface of the tube; and the stand of wire held in place on the tube using a bio-compatible bonding material.

53. An embolic filter assembly, said filter assembly comprising:

at least one strand of wire forming a support hoop;

the strand of wire extending from said support hoop and forming at least one suspension strut including at least two sections of the strand of wire proximal of an articulation point;

the suspension strut fixedly attached, at least in part, to a tube having a moveable guide wire or a moveable filter wire therethrough; and a blood permeable sac having an opening, said opening fixedly attached to the support hoop, thereby forming a proximal opening or mouth of the embolic filter;

wherein a bio-compatible bonding material is applied forming a common bead at the proximal ends of the at least two sections of the strand of wire; and the at least two sections of the strand of wire proximal of the articulation point positioned to the tube and held in place using a bio-compatible bonding material applied between the articulation point and the common bead.

54. An embolic filter assembly, said filter assembly comprising:

at least one strand of wire forming a support hoop;

the strand of wire extending from said support hoop and forming at least one suspension strut including at least two sections of the strand of wire proximal of an articulation point;

the suspension strut fixedly attached, at least in part, to a tube having a moveable guide wire or a moveable filter wire therethrough; and a blood permeable sac having an opening, said opening fixedly attached to the support hoop, thereby forming a proximal opening or mouth of the embolic filter;

wherein the at least two sections of the strand of wire proximal of the articulation point are intertwined; and the intertwined strand of wire proximal of the articulation point positioned to the tube and held in place using a bio-compatible bonding material.

55. An embolic filter assembly, said filter assembly comprising:

at least one strand of wire forming a support hoop;

the strand of wire extending from said support hoop and forming at least one suspension strut including at least two sections of the strand of wire proximal of an articulation point;

the suspension strut fixedly attached, at least in part, to a tube having a moveable guide wire or a moveable filter wire therethrough; and a blood permeable sac having an opening, said opening fixedly attached to the support hoop, thereby forming a proximal opening or mouth of the embolic filter;

wherein the tube is a thick-walled tube having an inside diameter substantially smaller than the outside diameter;

one or more holes having a diameter smaller than the diameter of the strand of wire are drilled into the distal end of the thick-walled tube;

the thick-walled tube heated to a temperature greater than the room temperature causing an increase in the diameter of the one or more holes;

the proximal ends of the strand of wire are placed with the one or more holes while the thick-walled tube is at the elevated temperature; and the thick-walled tube is cooled to room temperature causing a decrease in the diameter of the one or more holes forming a mechanical bond having the strand of wire securely held in place inside the one or more holes in the thick-walled tube.

56. An embolic filter assembly, said filter assembly comprising:

at least one strand of wire forming a support hoop;

the strand of wire extending from said support hoop and forming at least one suspension strut comprising at least two sections of the strand of wire forming the support hoop, the suspension strut having an articulation point whereafter the at least two sections of the strand of wire extend proximally for attachment to a guide wire or a filter wire;

the suspension strut coupled, at least in part, to the guide wire or the filter wire; and a blood permeable sac having an opening, said opening fixedly attached to the support hoop, thereby forming a proximal opening or mouth of the embolic filter;

wherein the at least one suspension strut is at least in part, entwined around said guide wire or said filter wire, thereby forming a helix around the guidewire or filter wire;

one or more regions on the at least two sections of the strand of wire proximal of the articulation point are stamped flat having one or more regions of unstamped wire therebetween;

the at least two sections of the strand of wire are intertwined and held in place by a bio-compatible bonding material forming a bonded strand of wire; and the bonded strand of wire is entwined around the guide wire or the filter wire, thereby forming the helix having the guide wire or the filter wire moveably passing through the lumen comprised by said helix.

57. An embolic filter assembly, said filter assembly comprising:

at least one strand of wire forming a support hoop;

the strand of wire extending from said support hoop and forming at least one suspension strut comprising at least two sections of the strand of wire forming the support hoop, the suspension strut having an articulation point whereafter the at least two sections of the strand of wire extend proximally for attachment to a guide wire or a filter wire;

the suspension strut coupled, at least in part, to the guide wire or the filter wire; and a blood permeable sac having an opening, said opening fixedly attached to the support hoop, thereby forming a proximal opening or mouth of the embolic filter;

wherein the at least one suspension strut is at least in part, entwined around said guide wire or said filter wire, thereby forming a helix around the guidewire or filter wire;

the at least two sections of the strand of wire proximal of the articulation point are intertwined together;

one or more regions on the intertwined wire proximal of the articulation point are stamped flat having one or more regions of unstamped wire therebetween;

the intertwined wire is held in place by a bio-compatible bonding material forming a bonded strand of wire; and the bonded strand of wire is entwined around the guide wire or the filter wire, thereby forming the helix having the guide wire or the filter wire moveably passing through the lumen comprised by said helix.

58. An embolic filter assembly, said filter assembly comprising:

at least one strand of wire forming a support hoop;

the strand of wire extending from said support hoop and forming at least one suspension strut comprising at least two sections of the strand of wire forming the support hoop, the suspension strut having an articulation point whereafter the at least two sections of the strand of wire extend proximally for attachment to a guide wire or a filter wire;

the suspension strut coupled, at least in part, to the guide wire or the filter wire; and a blood permeable sac having an opening, said opening fixedly attached to the support hoop, thereby forming a proximal opening or mouth of the embolic filter;

wherein the at least one suspension strut is at least in part, entwined around said guide wire or said filter wire, thereby forming a helix around the guidewire or filter wire;

the at least two sections of the strand of wire proximal of the articulation point are stamped flat;

the at least two sections of the flattened strand of wire are intertwined and held in place by a bio-compatible bonding material forming a bonded strand of wire; and the bonded strand of wire is entwined around the guide wire or the filter wire, thereby forming the helix having the guide wire or the filter wire moveably passing though the lumen comprised by said helix.

* * * * *